(12) United States Patent
Smith et al.

(10) Patent No.: US 10,918,831 B2
(45) Date of Patent: Feb. 16, 2021

(54) PRESSURE CATHETER AND CONNECTOR DEVICE

(71) Applicant: Laborie Medical Technologies, Corp., Mississauga (CA)

(72) Inventors: Bryce Smith, Sandy, UT (US); Ing Han Goping, Oakville (CA)

(73) Assignee: Laborie Medical Technologies Corp., Mississauga (CA)

( * ) Notice: Subject to any disclaimer, the term of this patent is extended or adjusted under 35 U.S.C. 154(b) by 267 days.

(21) Appl. No.: 15/456,062

(22) Filed: Mar. 10, 2017

(65) Prior Publication Data

US 2017/0259035 A1   Sep. 14, 2017

Related U.S. Application Data

(60) Provisional application No. 62/306,820, filed on Mar. 11, 2016.

(51) Int. Cl.
*A61M 25/00* (2006.01)
*A61M 39/10* (2006.01)
(Continued)

(52) U.S. Cl.
CPC ....... *A61M 25/0097* (2013.01); *A61B 5/0215* (2013.01); *A61B 5/036* (2013.01);
(Continued)

(58) Field of Classification Search
CPC ...... A61M 25/10184; A61M 25/10185; A61M 25/10186; A61M 25/1025; A61M 39/00;
(Continued)

(56) References Cited

U.S. PATENT DOCUMENTS 4,752,292 A   6/1988   Lopez et al.
5,573,007 A   11/1996  Bobo, Sr.
(Continued)

FOREIGN PATENT DOCUMENTS

CN   1859942 A    11/2006
EP   0774919 B1   11/2002
(Continued)

OTHER PUBLICATIONS

International Patent Application No. PCT/US2017/021893, Invitation to Pay Additional Fees and Partial Search Report dated Jun. 14, 2017, 16 pages.
(Continued)

*Primary Examiner* — David J. McCrosky
(74) *Attorney, Agent, or Firm* — Fredrikson & Byron, P.A.

(57) ABSTRACT

A connector apparatus for a pressure sensing catheter having a pressure-compliant member is disclosed. A first complementary connector has an aligning portion and a charging portion, with the aligning portion having a cross-sectional area less than a cross-sectional area of the charging portion. A second complementary connector has a proximal coupler with an alignment section and a charging section wherein, the alignment section having a cross-sectional area complementary to the cross-sectional area of the aligning portion to receive the alignment portion therein, the charging section having a cross-sectional area complementary to receive the charging portion and a resilient member therein. The first complementary connector can displace a volume of fluid from the proximal coupler into the pressure compliant member when the alignment section receives the aligning portion, the charging section receives the charging portion, and the resilient member forms the fluid tight seal within the charging section.

21 Claims, 21 Drawing Sheets

(51) Int. Cl.
*A61B 5/0215* (2006.01)
*A61B 5/00* (2006.01)
*A61B 5/03* (2006.01)

(52) U.S. Cl.
CPC .......... *A61B 5/6852* (2013.01); *A61B 5/6853* (2013.01); *A61M 39/10* (2013.01); *A61B 2562/225* (2013.01); *A61M 2025/0003* (2013.01)

(58) Field of Classification Search
CPC .......... A61M 39/0009; A61M 39/0018; A61M 39/10; A61M 39/1005; A61M 39/1011; A61M 39/1016; A61M 39/1027; A61M 2039/0009; A61M 2039/0018; A61M 2039/1005; A61M 2039/1016; A61M 2039/1027; A61M 25/0097; A61M 2025/0003; A61M 25/001; A61B 5/6853; A61B 5/0215; A61B 2562/225; F16L 21/007
USPC .......... 600/561, 587; 604/533–539; 285/9.2, 285/376, 399, 401, 402
See application file for complete search history.

(56) References Cited

U.S. PATENT DOCUMENTS

| | | | |
|---|---|---|---|
| 5,776,116 A | 7/1998 | Lopez et al. | |
| 5,795,325 A | 8/1998 | Valley et al. | |
| 6,421,013 B1 | 7/2002 | Chung et al. | |
| 6,649,829 B2 | 11/2003 | Garber et al. | |
| 6,673,022 B1 | 1/2004 | Bobo et al. | |
| 7,352,771 B2 | 4/2008 | Garber | |
| 7,926,856 B2* | 4/2011 | Smutney | A61M 39/10 285/330 |
| RE44,310 E | 6/2013 | Chadbourne et al. | |
| 8,454,579 B2* | 6/2013 | Fangrow, Jr. | A61M 39/26 604/539 |
| 9,541,227 B2* | 1/2017 | Okiyama | A61M 39/045 |
| 10,500,391 B2* | 12/2019 | Takeuchi | A61M 39/16 |
| 2004/0127813 A1 | 7/2004 | Schwamm | |
| 2005/0064223 A1 | 3/2005 | Bavaro et al. | |
| 2005/0187430 A1 | 8/2005 | Aundal et al. | |
| 2005/0215119 A1 | 9/2005 | Kaneko | |
| 2007/0073270 A1 | 3/2007 | Christensen | |
| 2007/0252771 A1 | 11/2007 | Maezawa et al. | |
| 2007/0273525 A1 | 11/2007 | Garber et al. | |
| 2008/0030343 A1 | 2/2008 | Raybuck et al. | |
| 2009/0009290 A1 | 1/2009 | Kneip et al. | |
| 2009/0171278 A1 | 7/2009 | Hirszowicz et al. | |
| 2009/0306539 A1 | 12/2009 | Woodruff et al. | |
| 2010/0001516 A1 | 1/2010 | Pisula, Jr. et al. | |
| 2010/0249663 A1 | 9/2010 | Nishtala | |
| 2010/0249723 A1 | 9/2010 | Fangrow, Jr. | |
| 2011/0136550 A1 | 6/2011 | Maugars | |
| 2011/0152841 A1 | 6/2011 | Nemoto | |
| 2011/0210541 A1 | 9/2011 | Lewis et al. | |
| 2013/0184612 A1 | 7/2013 | Quackenbush et al. | |
| 2013/0268029 A1 | 10/2013 | Cauller et al. | |
| 2013/0270820 A1* | 10/2013 | Py | A61M 39/10 285/330 |
| 2014/0203077 A1 | 7/2014 | Gadh et al. | |
| 2014/0266775 A1 | 9/2014 | Moon et al. | |
| 2015/0130408 A1 | 5/2015 | Wei | |
| 2015/0135502 A1 | 5/2015 | Rankin et al. | |
| 2015/0250974 A1 | 9/2015 | Bobo, Sr. et al. | |
| 2016/0029912 A1 | 2/2016 | Stimpson | |
| 2016/0046130 A1 | 2/2016 | Burdge et al. | |
| 2016/0089254 A1 | 3/2016 | Hopkinson et al. | |
| 2016/0213228 A1 | 7/2016 | Rohl et al. | |
| 2017/0021144 A1 | 1/2017 | Kanner et al. | |
| 2017/0140330 A1 | 5/2017 | Rinzler et al. | |
| 2017/0209682 A1 | 7/2017 | Shemesh | |
| 2017/0258345 A1 | 9/2017 | Smith | |
| 2017/0266429 A1* | 9/2017 | Striggow | A61M 5/142 |

FOREIGN PATENT DOCUMENTS

| | | |
|---|---|---|
| EP | 1996851 B1 | 11/2011 |
| EP | 1799610 B1 | 11/2012 |
| EP | 1866611 B1 | 9/2014 |
| WO | 2005032639 A1 | 4/2005 |
| WO | 2005107006 A1 | 11/2005 |
| WO | 2009055435 A1 | 4/2009 |

OTHER PUBLICATIONS

International Patent Application No. PCT/US2017/021893, International Search Report and Written Opinion dated Aug. 18, 2017, 19 pages.
Bryce Smith, U.S. Appl. No. 15/456,002, filed Mar. 10, 2017, entitled "Pressure Catheter Device," 32 pages.
English Abstract for Chinese Publication No. CN 1859942 A, published Nov. 8, 2006, 1 pgs.
Yamashita, Noboru et al. "Preparation and characterization of gelatin sponge millispheres injectable through microcatheters", Medical Devices: Evidence and Research, 2009:2 19-25, 7 pgs.

* cited by examiner

US 10,918,831 B2

PRESSURE CATHETER AND CONNECTOR DEVICE

RELATED APPLICATIONS

This application claims the benefit of U.S. Provisional Patent Application No. 62/306,820 filed Mar. 11, 2016, the contents of which are incorporated herein by reference.

BACKGROUND

Pressure catheter devices can be used for the measurement and analysis of pressure within a body cavity. Such devices typically include an elongate catheter having at least one gas-filled pressure monitoring lumen extending longitudinally through the catheter. A gas-filled membrane (e.g., a balloon) can be formed on the outer surface of the catheter. The gas-filled membrane can be in fluid communication with the gas-filled pressure monitoring lumen. Changes in pressure against the gas-filled membrane may result in changes in pressure of the gas within the gas-filled pressure monitoring lumen. A pressure transducer connected to the proximal end of the gas-filled pressure monitoring lumen can sense and display or record the changes in pressure which can be communicated through the gas-filled pressure monitoring lumen of the catheter.

Some such pressure catheters may be connected by complementary connectors to permit charging the gas-filled membrane. For instance, engagement of complementary connectors may displace a volume of fluid and thereby charge the gas-filled membrane. Some known pressure catheter and connector devices have moving components that can become clogged with fluids or other biological materials after repeated use. In addition, such devices may require multiple steps to connect complementary connectors and charge the catheter.

SUMMARY

In one aspect, this disclosure provides a connector apparatus and pressure sensing catheter system, comprising a catheter and a connector assembly. The catheter comprises an elongate member and at least one monitor lumen in fluid communication with a pressure-compliant member located about an exterior distal end of the elongate member. The connector assembly comprises a first complementary connector having a pressurizing device. At least portions of the monitor lumen extend through the first complementary connector. The connector assembly includes a second complementary connector with a connector interface sized to be engageable with the pressurizing device. When the pressurizing device of the first complementary connector engages with the connector interface of the second complementary connector, the pressurizing device displaces a volume of fluid within the connector interface into the monitor lumen of the elongate member so as to charge the pressure compliant members.

In another aspect, the first complementary connector includes a resilient member disposed on an external surface of the first complementary connector, and a protrusion. The second complementary connector includes a plurality of channels configured to receive at least a portion of the protrusion of the first complementary connector therein so as facilitate engagement of the first complementary connector and the second complementary connector, and thereby permit charging the one or more hollow pressure compliant members with a volume of fluid. Further, a pressure detection device is disposed at the base of the second complementary connector so as to be housed therewithin and fluidly coupled to the one or more hollow pressure compliant members so as to detect a pressure thereof.

In a further aspect, the first complementary connector comprises a first lumen and a second lumen, each being disposed within an interior of the first complementary connector. The second complementary connector comprises a first chamber the fluidly connectable to the pressurizing device, and a second chamber in fluid communication with the first chamber. The first lumen and the second lumen of the first complementary connector can be in fluid communication with a first lumen and a second lumen of the elongate member, respectively. The first complementary connector can be configured to displace a predetermined volume of fluid from the first chamber into the first lumen of the elongate member, and a predetermined volume of fluid from the second chamber into the second lumen of the elongate member while the first complementary connector is connected to the second complementary connector.

In a further aspect a method of charging a multi-channel pressure detection device catheter, can include the step of providing a pressure catheter device and connector assembly according to any of the embodiments disclosed herein. The method can include the step of connecting the first complementary connector with the second complementary connector, and thereby use the first complementary connector to displace a predetermined volume of fluid from within the second complementary connector into one or more monitor lumens so as to charge the pressure compliant members of the catheter.

The details of one or more examples are set forth in the accompanying drawings and the description below. Other features, objects, and advantages will be apparent from the description and drawings, and from the claims.

DETAILED DESCRIPTION

For purposes of illustrating the various aspects of the methods and systems claimed herein, the discussion below will be directed to describing exemplary embodiments used in urodynamic pressure sensing, as further described in the commonly-assigned application U.S. Ser. No. 15/456,002, filed on Mar. 10, 2017, titled "PRESSURE CATHETER DEVICE," the entire contents of which are hereby incorporated by reference. It should be noted, however, that the elements and principles discussed herein are applicable to other applications. For example, the exemplary embodiments described herein are contemplated for use with any type of catheter wherein measurement of pressure within the body of a patient is desired. Further, discussion of methods and systems herein can be interchangeable with respect to specific aspects. In other words, specific discussion of one method or system (or components thereof) herein is equally applicable to other aspects as they relate to the system or method, and vice versa.

Figure 1:
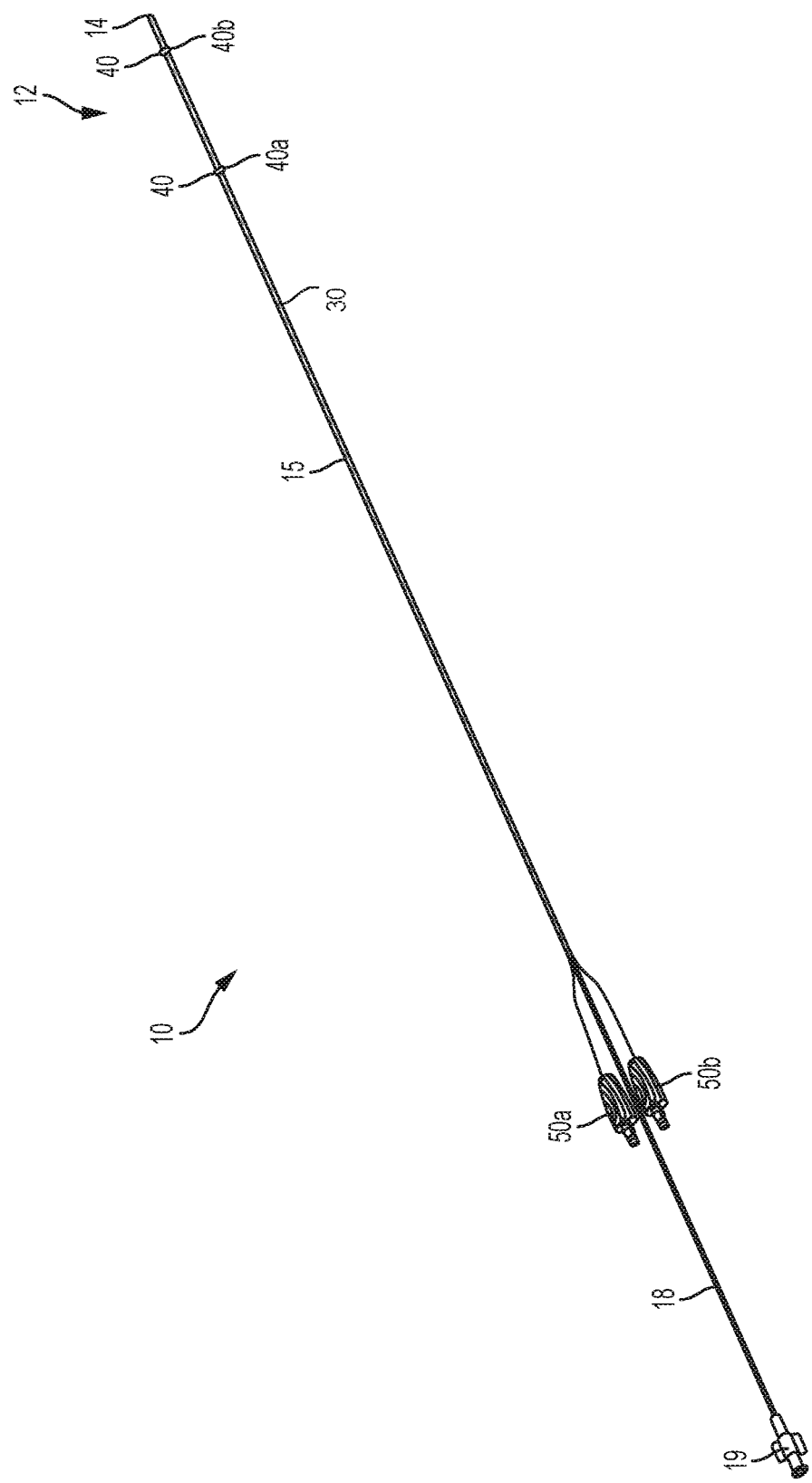
FIG. 1 is a perspective view of a pressure catheter in accordance with a non-limiting exemplary embodiment.

FIG. 1 is a perspective view of a pressure catheter in accordance with a non-limiting exemplary embodiment. As shown in FIG. 1, a pressure monitoring catheter 10 The distal end 12 of the catheter 10 comprises a soft, pliant tip 14 which facilitates insertion of the catheter 10 into the patient. The soft tip 14 may preferably be formed of a material which is pliant enough to deflect or give as the tip 14 encounters a resistive force, such as the wall of the bladder. A low durometer plastic or elastomer, such as polyvinyl chloride (PVC) or a polyurethane, is suitable though other materials having a suitable rigidity/pliancy and are safe for use inside the cavity or vessel of a subject or patient can be used.

With continued reference to FIG. 1, the tip 14 is formed from an elongated hollow tube 15 which extends from the tip 14 at its distal end to one or more first complementary connector 50 on its proximal end. The hollow tube 15 is formed of flexible, biocompatible material, such as PVC or a polyolefin, with sufficient properties, such as wall thickness, to resist collapse under normal conditions, and sized in length to extend from within a cavity (e.g., the alimentary canal or urinary tract) of a patient to outside the body of the patient.

As seen from FIG. 1, one or more flaccid, pressure-compliant members (e.g., a medical grade balloon or bladder used in medical applications) 40 are located on a distal end 12 of the catheter 10. The balloons 40 are configured to receive a predetermined volume of fluid in order to provide resistance to induced pressure forces acting externally on the balloon 40. The induced pressure forces are transmitted through the balloon 40 and down a monitor lumen within the catheter 10 and measured by a connector assembly. An elongate center arm 18 extends from the proximal end 11 of the catheter 10 to a connector 19. The connector 19 in turn can be used to attach a syringe or other device used for the collection (e.g. aspiration) or delivery (e.g. infusion) of fluids to or from the cavity of the patient.

Upon insertion of the catheter 10 into the body cavity, the balloon 40 is in a substantially deflated state. With charging, the balloon 40 becomes at least partially filled with fluid (e.g., air). Thus, depending on how much fluid is present in the balloon 40 prior to charging, the balloon 40 may be filled between about 40% and about 70% of its capacity following charging. Advantageously, balloon 40 may not be overfilled so as to not introduce the structure of the balloon 40 into the signal. In other words, the flaccidity of the partially-filled working volume of balloon 40 can reduce aberrant effects in pressure detection due to temperature changes (e.g., from Charles's Law), or other aberrant effects which may introduce signal artifacts due to the balloon wall internal forces, or external balloon compression from debris.

The low durometer material of the balloon 40 allows the surface of the balloon 40 to deform with an increase in pressure. Therefore, an increase in body cavity pressure ranging from 2 mmHg to 200 mmHg will deform the balloon 40 and, in turn, modify the pressure in the fluid column within the balloon 40 and the secondary (or monitor) lumen 30. The change in pressure is translated down the fluid column to the diaphragm of the pressure detection device. Deflection of the diaphragm resulting from an increase in pressure is converted to an electrical signal by the transducer and is relayed to the monitor through the cable or wirelessly. Similarly, a subsequent decrease in body cavity pressure is also relayed by subsequent expansion of the balloon 40.

As shown in FIG. 1, two balloons 40a and 40b are disclosed and are connected each through a separate monitor lumen to respective first complementary connector 50a and 50b. Accordingly, in some examples, a fluid column can be defined by fluid (e.g., air) within the monitor lumen (including the monitor lumen within the first complementary connector 50) and the balloon 40. The fluid columns (for instance, defined in the monitor lumen and internal balloon volume) of each balloon 40a, 40b may not be in fluid communication with one another. Rather, balloons 40a and 40b can be independently charged by connection of respective complementary connector assemblies. For instance, in FIG. 1, a first complementary connector 50a and a corresponding second complementary connector may be used to charge the fluid column associated with balloon 40a, while first complementary connector 50b and a corresponding female complementary connector can be used to charge fluid column associated with balloon 40b.

Figure 2:
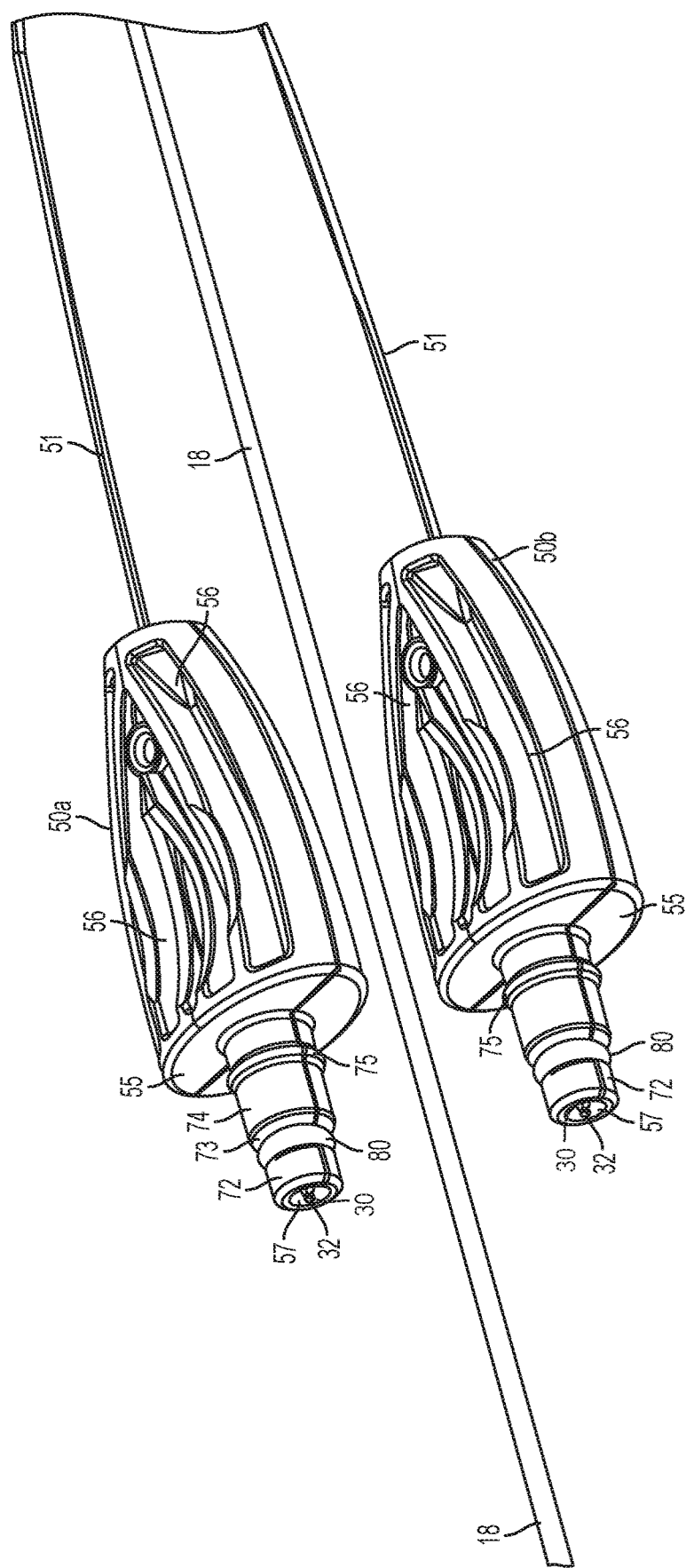
FIG. 2 is a close up perspective view of a first complementary connectors associated with the pressure catheter of FIG. 1.
Figure 3:
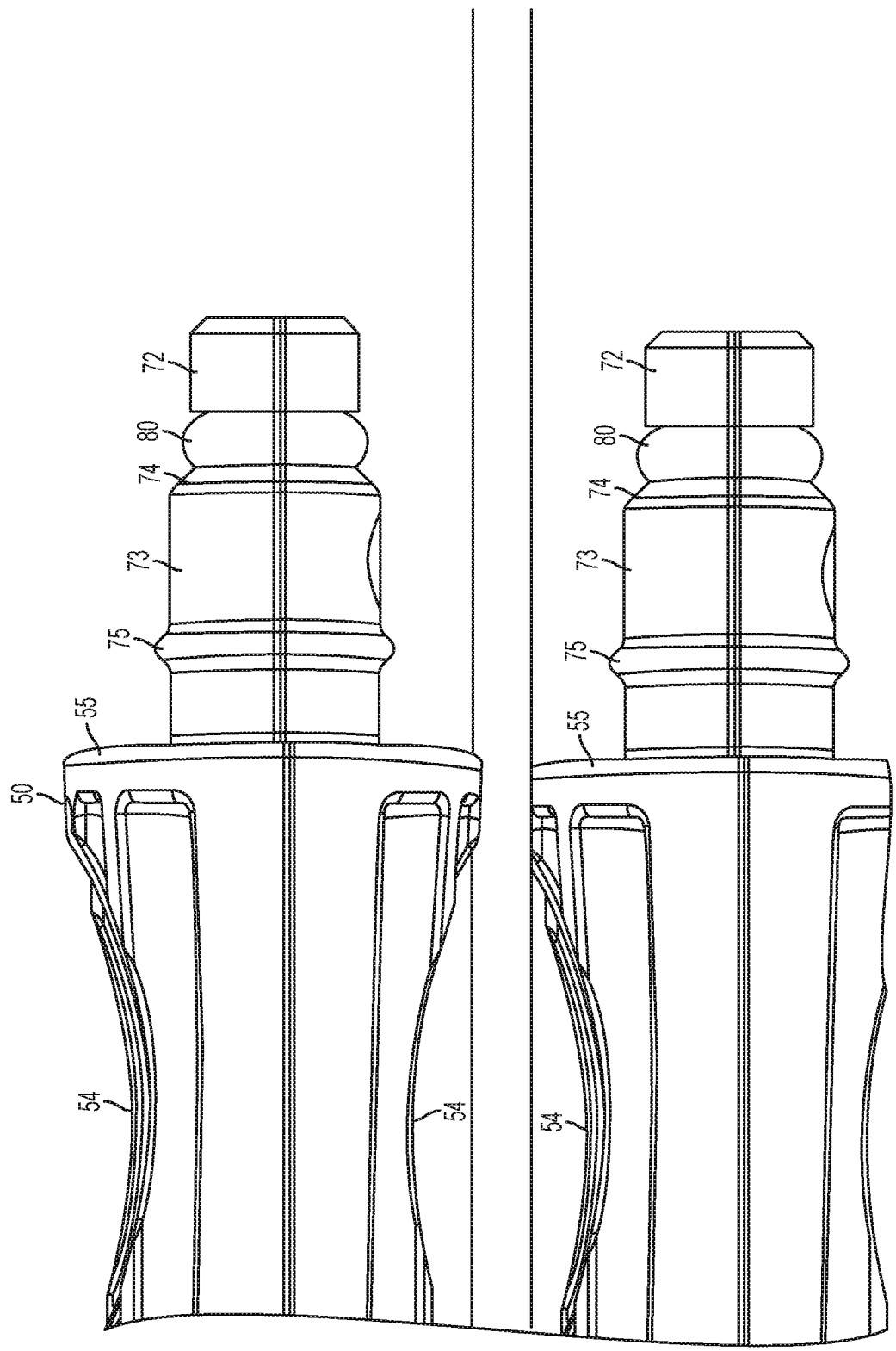
FIG. 3 is a close up side view of the first complementary connectors of FIG. 2.

FIGS. 2 and 3 illustrate details of a representative first complementary connector 50 (e.g., 50a and 50b). As perhaps best seen in FIG. 3, the first complementary connector 50 comprises an indentation 54 on the front and back sides of the first complementary connector 50 and further comprises a plurality of grooves 56 (best seen in FIG. 2) disposed therein. The first complementary connector 50 can, in some examples, be a male connector, having a pressurizing device 72 (e.g. piston or plunger) projecting therefrom. In such cases, at least portions of the pressurizing device 72 (e.g., charging portion 73) can be sized so as to permit a complementary connection with a second complementary connector, as will be discussed further below.

In some advantageous examples, the first complementary connector can have a distal portion with a variable cross-sectional area to align with a second complementary connector. For instance, the variable cross-section portion can include an aligning portion 57, a charging portion 73 and an engagement portion 75. In some such examples, a resilient member 80 can be positioned between the aligning portion 57 and the charging portion 73 (e.g., on the ramp portion 74) so as to form a fluid tight seal when connected with the second complementary connector. In some such examples, the resilient member 80 can comprise an O-ring to permit a fluid tight connection.

As seen from FIGS. 2 and 3, the aligning portion 57 can have a cross-sectional area that differs from the charging portion 73 and the engagement portion 75 respectively. For instance, the aligning portion 57 can have a cross-sectional area less than the cross-sectional area of both the charging portion 73 and the engagement portion 75. Advantageously, this may permit insertion of the resilient member 80 through the aligning portion 57 so as to position it near the ramp portion 74. In some such cases, the ramp portion 74 can have a cross-sectional area those transitions from the cross-sectional area of the aligning portion 57 to the cross-sectional area of the engagement portion 75. The engagement portion 75 can be in the form of a protrusion, whereby the engagement portion 75 has a cross-sectional area greater than the cross-sectional area of both the aligning portion 57 and the charging portion 73.

Figure 4:
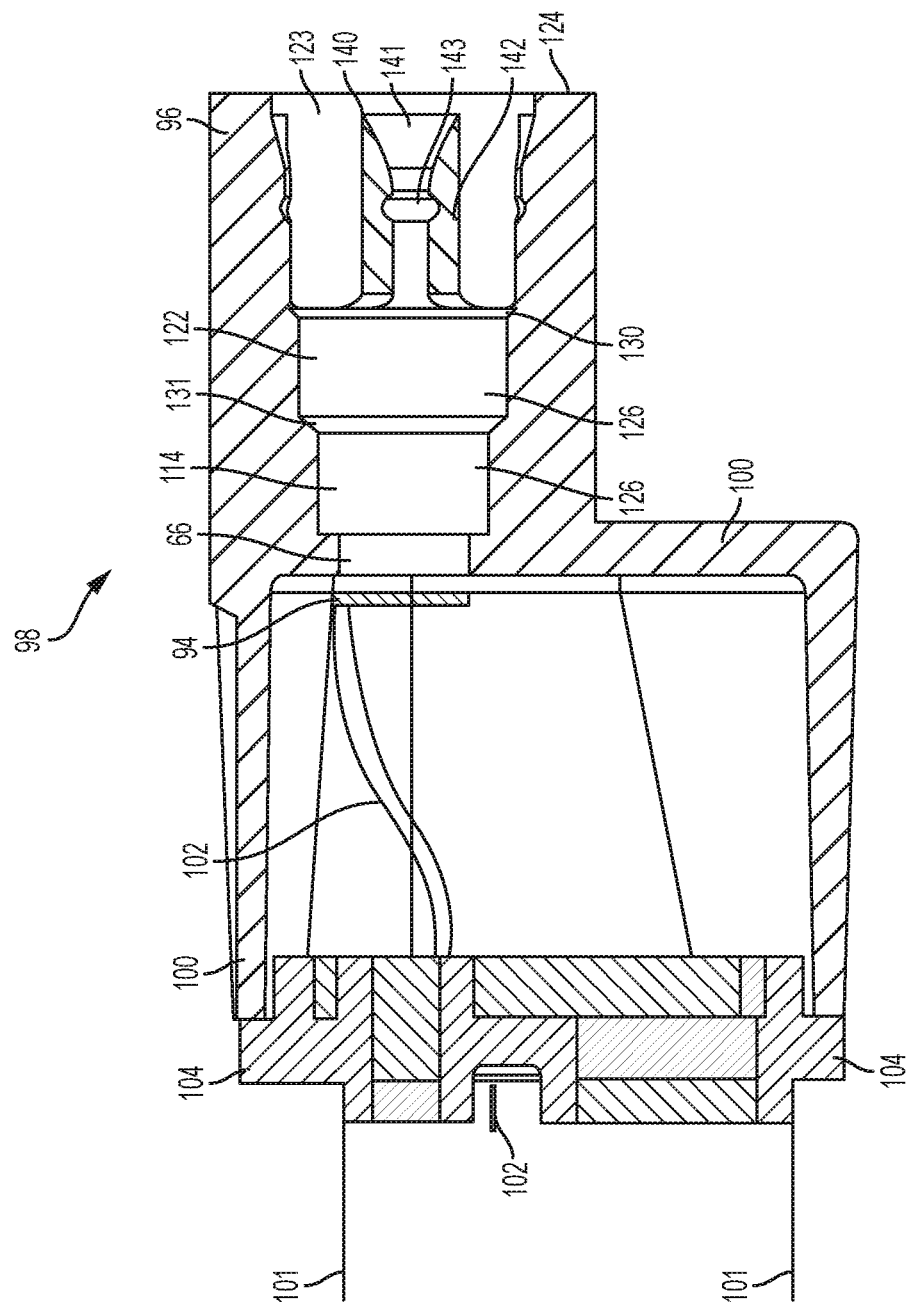
FIG. 4 is a cross sectional side view of a second complementary connector in accordance with a non-limiting exemplary embodiment.
Figure 5:
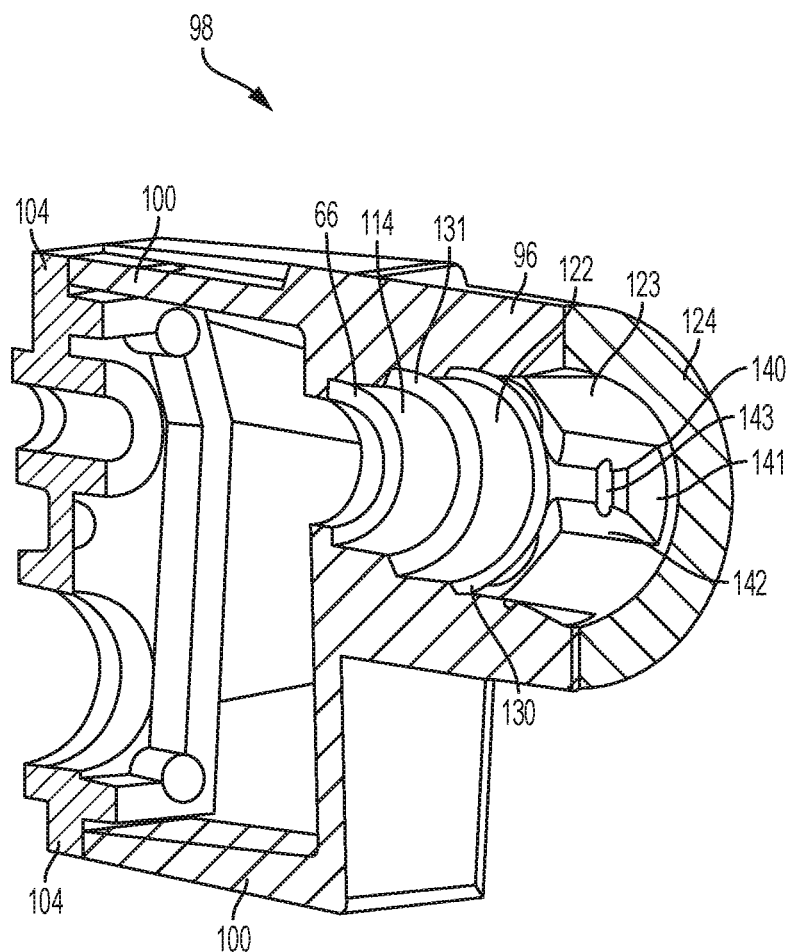
FIG. 5 is a perspective cross sectional view of a second complementary connector in accordance with a non-limiting exemplary embodiment.
Figure 6:
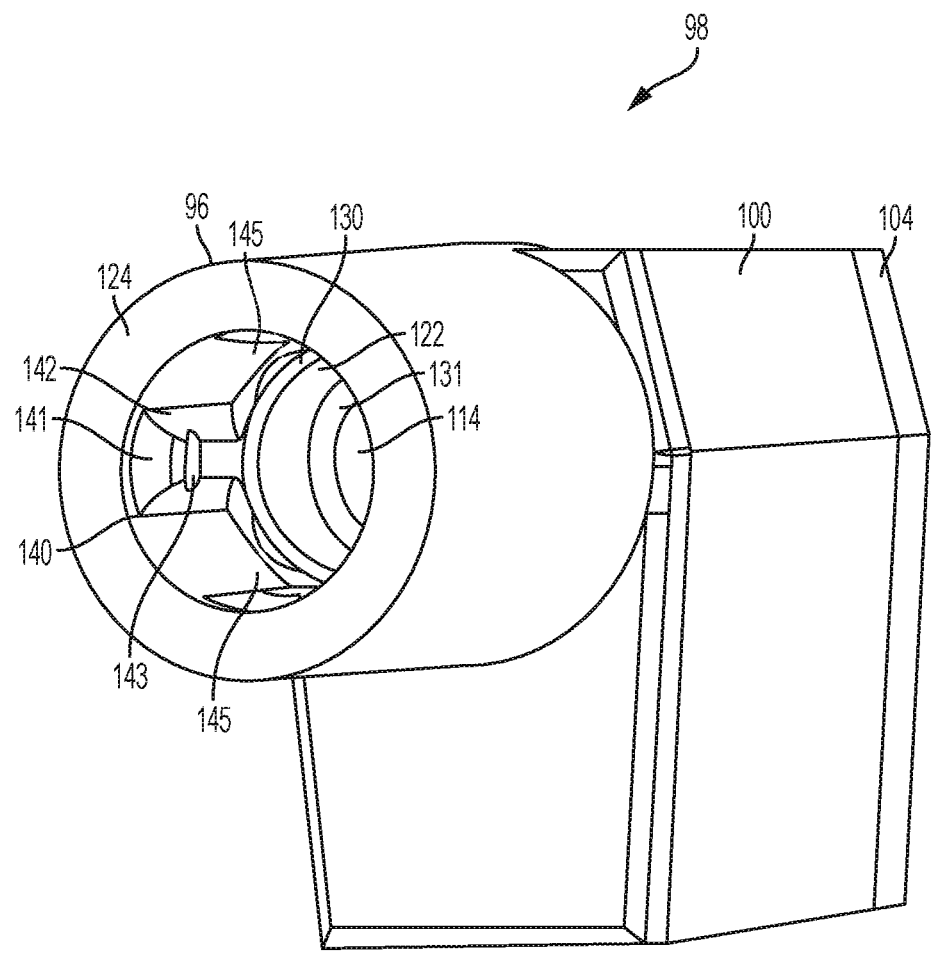
FIG. 6 is a perspective view of a second complementary connector in accordance with a non-limiting exemplary embodiment.

FIGS. 4 and 5 illustrate sectional views of a second complementary connector according to some examples. The second complementary connector 98 comprises a proximal coupler 96 extending from an enclosure 100. The proximal coupler 96 can have a alignment section 114 for engaging with the pressurizing device 72. In some examples, the alignment section 114 can be a female connector having a bore or a cavity sized in internal diameter and length to frictionally receive the distal portion of the first complementary connector 50. For instance, proximal coupler 96 can be sized such that certain portions of the first complementary connector are received therewithin. A pressure detection device 94 therein can be housed within the enclosure 100. An end cap 104 can close the enclosure 100.

As described previously, with reference to FIGS. 3 and 4, when the first complementary connector 50 is connected to the second complementary connector 98, fluid column associated with the monitor lumen 30 (illustrated by dashed lines in FIG. 1) and the balloon 40 (not shown in FIGS. 3 and 4) may be displaced, resulting in a "charge volume" of fluid for charging the balloon. In accordance with a non-limiting exemplary embodiment, first and second complementary connectors 50, 98 are operably connectable to one another to not only create the "charge volume" introduced into the catheter 10, but also to provide pressure measurement transmitted through the balloon 40 and the monitor lumen. As noted herein, the charge volume refers to the total amount of fluid introduced into the fluid (e.g., air) column to "charge" or ready the catheter 10 for pressure measurement.

In certain embodiments, the pressure detection device 94 can be a diaphragm pressure detection device, piezoelectric pressure detection device and the like. When the first complementary connector and the second complementary connector 98 are connected to each other, the pressure detection device can interface (e.g., be in fluid communication) with the fluid column of the catheter 10 to detect changes in pressure acting on the balloon 40 (e.g., urodynamic pressure).

The second complementary connector 98 (and in turn, catheter 10 connected thereto by the complementary connection of the first complementary connector) can be detachably attached to a cable assembly, and can be coupled (either wired or wirelessly) to a processor and monitor. In one aspect where the cable assembly comprises a wired reusable assembly, the reusable assembly can have, at its proximal end, an electrical connector configured to be connected to a processor and monitor. In such embodiments, the pressure detection device 94 can be coupled to a data/power cable 101 of a reusable interface cable assembly to transmit pressure measurements to the processor. A protective cover 108 may be provided on the reusable interface cable assembly sized to fit over the second complementary connector 98.

While a first complementary connector 50 is shown as being attached to the catheter 10 connectable to a separate second complementary connector 98, in an alternative arrangement, the second complementary connector 98 could be coupled to the catheter 10 being connectable to a separate first complementary connector 50. In that arrangement, the pressure detection device 94 and the monitor lumen 30 (illustrated by dashed lines in FIG. 1, a portion of which is visible in FIG. 2) could both form part of the second complementary connector 98 and the first complementary connector 50 may act as a plunger and electrical connector to the pressure detection device 94. For instance, an electrical contact present on the first complementary connector 50 may couple with an electrical contact on the second complementary connector 98 to transmit both power to the pressure detection device 94 and data from the pressure detection device 94 to a processor and/or monitor. Accordingly, a wired connection or wireless transmitter connects the pressure detection device to a processor and monitor and/or database.

Reference is made to FIGS. 3 and 5 to describe the complementary connection between the first complementary connector and the second complementary connector and the concomitant charging of the balloons. Upon insertion of the pressurizing device 72 in the alignment section 114 of the second complementary connector 98, the O-ring 80 becomes seated against an inner wall of the alignment section 114 to form a fluid-tight fit. The proximal extremity 66 of the enclosure 100 and the open proximal end 32 of the monitor lumen 30 are positioned in close proximity to the pressure detection device 94 retained within the enclosure 100, so as to minimize dead space in the system. The pressure detection device 94 may be, in a non-limiting example, a pressure transducer having a deformable diaphragm positioned toward the alignment section 114 of the proximal coupler 96. Wiring 102 extends from the pressure detection device 94 through the enclosure 100 and to the proximal end of the cable 101 for communication to a processor.

Continuing with FIGS. 3 and 5, the second complementary connector comprises an alignment section 114 that can receive the aligning portion 57 of the first complementary connector 50. Further, the second complementary connector comprises a charging section 122 that can receive the charging portion 73 of the first complementary connector 50. The second complementary connection also includes an engagement section 123 at least portions of which can engage with the engagement portion 75 of the first complementary connector 50. In some embodiments, the engagement section 123 can be a "vent section" having vents to permit venting of fluids and reduce the chances of the balloons from being overcharged, as will be described further below.

As seen from FIGS. 3, 4 and 5, the alignment section 114, the charging section 122 and the engagement section 123 can have cross-sectional areas that differ from each other. Advantageously, the cross-sectional areas of alignment section 114, the charging section 122 and the engagement section 123 are complementary to the cross-sectional areas of the aligning portion 57, charging portion 73 and the engagement portion 75 of the first complementary connector 50, so as to form a mating connection therewith. Further, some such embodiments permit ease of alignment (e.g., coaxial) of the proximal coupler 96 and the distal portion of the first complementary connector 50, so as to make efficient use of available space and reduce inaccuracies of pressure measurement (for instance, by positioning the proximal end 32 of the monitor lumen 30 close to and axially aligned with the pressure detection device 94).

The alignment section 114 and charging section 122 lying between the engagement section 123 of the proximal coupler 96 define an internal space 126 which contains a predetermined or selected volume of fluid (e.g., the charge volume) prior to insertion of the pressurizing device 72 into the proximal coupler 96 of second complementary connector 98. Thus, as the pressurizing device 72 is inserted like a plunger with its aligning portion 57 received into the alignment section 114 of second complementary connector 98, part of the volume of fluid contained within the internal space 126 of the alignment section 114 is displaced by pressurizing device 72 through the end 32 of monitor lumen 30 adding the volume of fluid to the fluid column. The displaced volume of fluid can be sufficient to "charge" or partially fill the balloon 40 with an appropriate amount of fluid to expand the balloon 40 to function with desired sensitivity responsive to a given range of pressure values. In other words, the effective fluid volume trapped in the fluid column can be defined by the inward stroke or travel of pressurizing device 72 from the point at which O-ring 80 passes flutes 130 until pressurizing device 72 is fully inserted in second complementary connector 98 and the O-ring 80 is seated within the alignment section 114 slightly past flutes 131. In addition, when the pressurizing device 72 is fully inserted, the face 124 of the second complementary connector 98 can be seated against the face 55 of the first complementary connector 50. In a non-limiting exemplary embodiment, the front face of the pressurizing device 72 comprises a cup or a void containing a predetermined volume of fluid.

In the illustrated embodiments (best seen in FIGS. 2 and 3), the aligning portion 57 of the pressurizing device 72 has an outer diameter substantially similar to the inner diameter of alignment section 114 such that when inserted within alignment section 114, the corresponding surfaces of the aligning portion 57 and the alignment section 114 are frictionally engaged. The charging portion 73 of the first complementary connector 50 is sized such that its outer diameter is substantially similar to the inner diameter of charging section 122. When the aligning portion 57 is received into alignment section 114, the ramp portion 74 of charging portion 73 rests against the flutes 131 of the second complementary connector 98. The outer diameter of the O-ring 80 is sized slightly larger than the inside diameter of the charging section 122 so that it engages the side walls of the charging section 122 and, under compression, forms a seal against the volume of fluid between the O-ring 80 and the end of the alignment section 114. In this manner, as the O-ring 80 is advanced with the proximal coupler 96, the "charge volume" of fluid is pushed into the monitor lumen 30.

FIGS. 4-8 illustrate a second complementary connector according to different embodiments. In some such examples, referring to FIGS. 4 and 5, the engagement section 123 of proximal coupler 96 has a plurality of raised platforms 140 disposed about its inside surface at predetermined circumferential locations. The raised platforms 140 are rectangular (though they may comprise other shapes) and include tapered front surfaces 141 to accommodate placement of the pressurizing device 72 and charging portion 73 (seen in FIG. 2) of the first complementary connector 50 within the proximal coupler 96. Returning to FIG. 4, the platforms 140 further have tapered side surfaces 142. A channel 143 is disposed near a center of the platform 140. The channel 143 extends in a direction normal to the longitudinal length of the platform 140 and is placed at certain circumferential directions (e.g., 0 degrees, 90 degrees, 180 degrees and 270 degrees). Alternatively, the channel 143 can extend continuously over the circumference of the engagement section 123.

In some such examples, the channel 143 is perpendicular to the direction in which the pressurizing device 72 is inserted into the proximal coupler 96. Each of the channels 143 are coplanar within the engagement section 123 and are constructed with a width approximately equal to a width of the engagement portion 75 located on the charging portion 73 of the first complementary connector 50.

With continued reference to FIGS. 2 and 4, when the pressurizing device 72 and charging portion 73 of first complementary connector 50 are inserted within the alignment section 114 and charging section 122 of the second complementary connector 98, respectively, the engagement portion 75 seats within the channels 143 located in the raised platforms 140 acting as a locking mechanism. Advantageously, the locking mechanism does not require moving parts or may not be exposed to liquids. For instance, because the engagement portion 75 is fully enclosed within the proximal coupler 96, it may not be exposed to extraneous materials that may interfere with the locking capability of the connector assembly. Moreover, as the engagement portion 75 seats within channels 143 it creates an audible "click" indicating to the user that the connection has been made. In addition, the force associated with advancement of the engagement portion 75 within the channels 143 may result in a vibration once the connection is made, creating a tactile indication to the user.

Referring again to FIGS. 2 and 4, during placement of the pressurizing device 72 and charging portion 73 into the proximal coupler 96, the space between the raised platforms 140 in the engagement section 123, shown generally at 145, acts as a vent for fluid within the proximal coupler 96 that may not form part of the "charged volume" within the alignment section 114 and charging section 122. For instance, as the pressurizing device 72 and charging portion 73 are placed into the proximal coupler 96, but prior to the O-ring's engagement with the side surface of the charging section 122, fluid displaced from the proximal coupler 96 by the pressurizing device 72 and charging portion 73 passes by a side surface of the pressurizing device 72 and charging portion 73 and through the vent 145. Further, in some such cases, the balloons 40 may not be charged (e.g., by displacement of fluid) until an adequate fluid seal is established between the first complementary connector and the second complementary connector, for instance, until the O-ring 80 engages at a predetermined axial position (e.g., past flutes 131) on the side surface of the charging section 122. Accordingly, the specific volume of fluid to properly "charge" the balloon 40 is introduced into the fluid column. Advantageously, such embodiments may reduce the chances of overcharging the balloon 40.

Figure 7A:
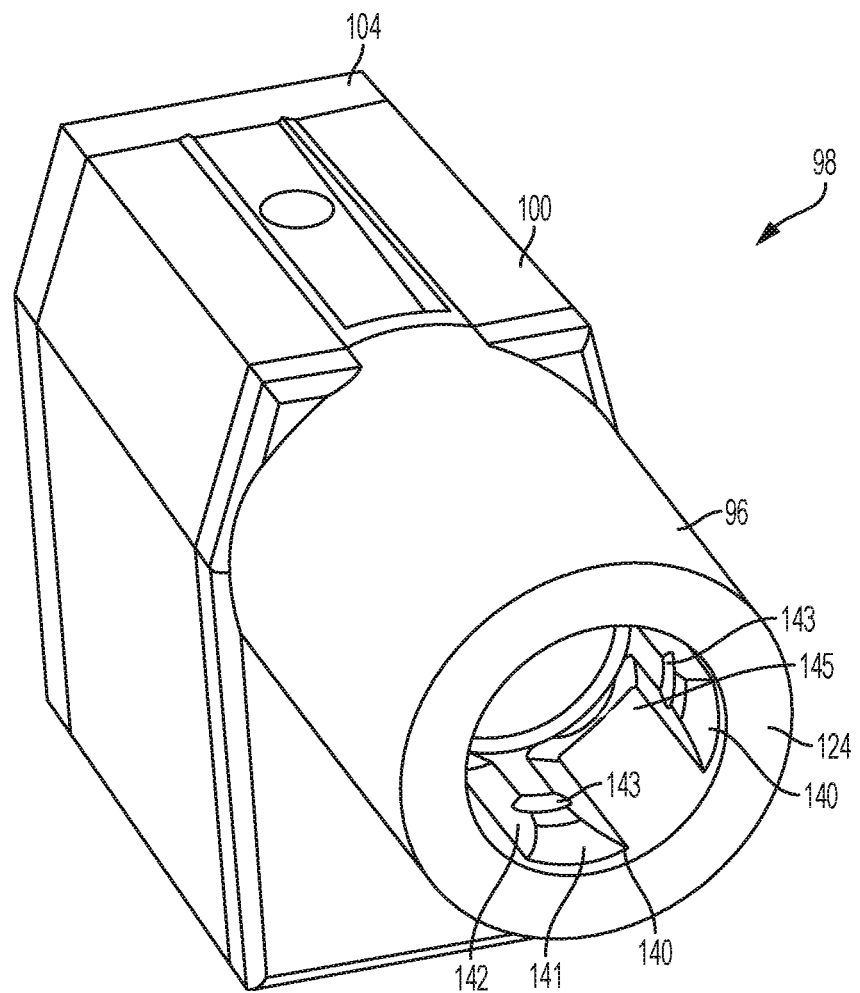
FIG. 7A is another perspective view of a second complementary connector in accordance with a non-limiting exemplary embodiment.
Figure 7B:
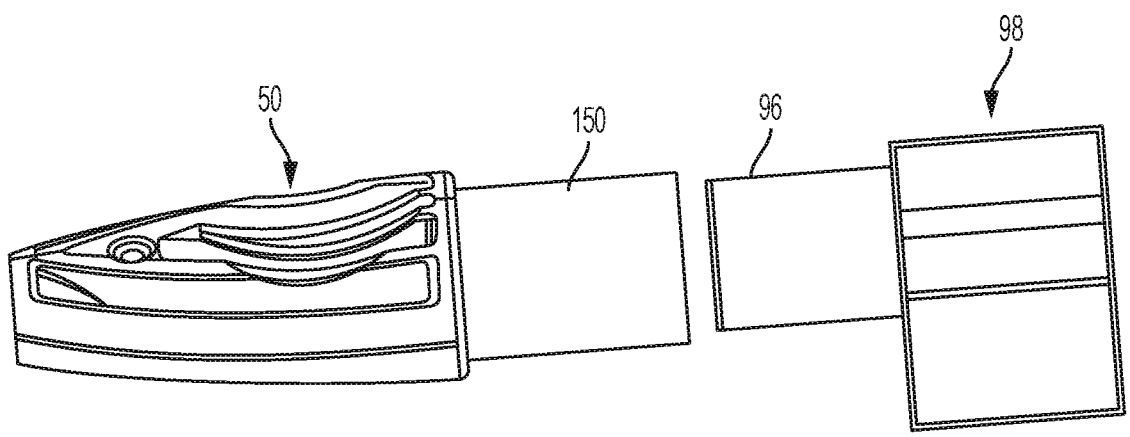
FIGS. 7B, 7C, 7D and 7E illustrate a perspective view and a cross-sectional view of a first complementary connector and a second complementary connector according to another non-limiting exemplary embodiment.
Figure 7C:
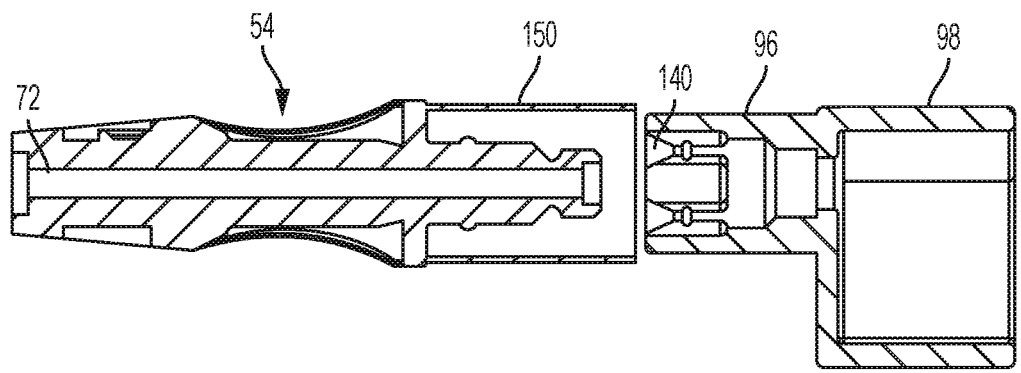

FIGS. 7B-7E illustrate various views of the first complementary connector 50 and the second complementary connector 98. In FIGS. 7B and 7C, a fluid resistant cover is provided on the first complementary connector. The fluid resistant cover 150 generally surrounds the pressurizing device 72. When connected to the second complementary connector 98, the fluid resistant cover 150 can fluidly isolate components of the first and second complementary connectors to fluid ingress. For instance, the fluid resistant cover 150 can isolate water of other bodily fluids from entering components of the first and second complementary connectors (e.g., pressure detection device 94 housed therewithin).

Figure 7D:
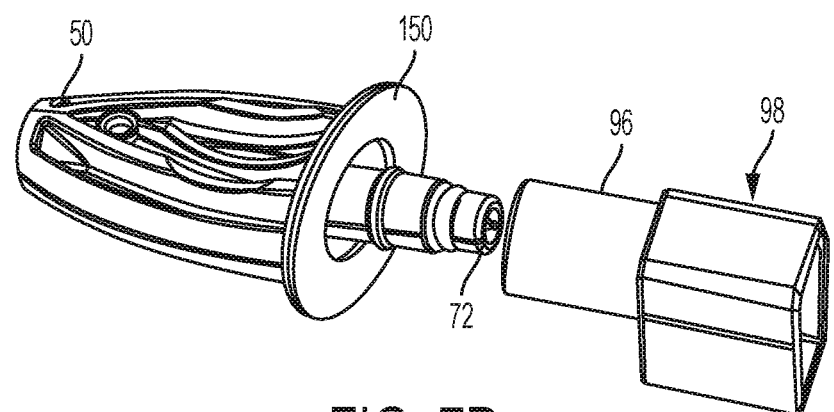
Figure 7E:
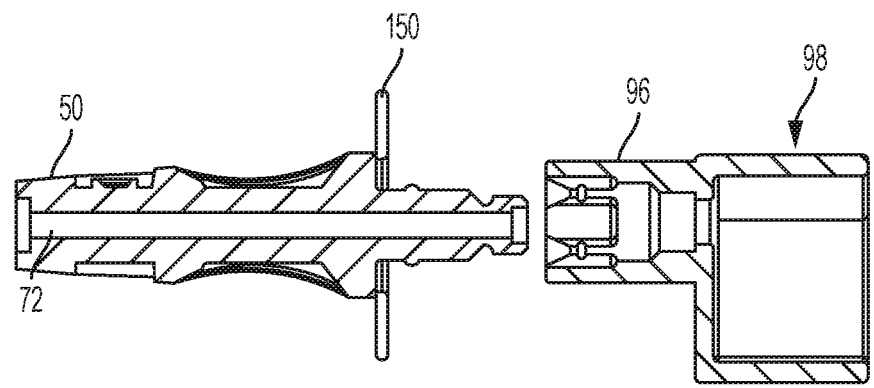
Figure 8:
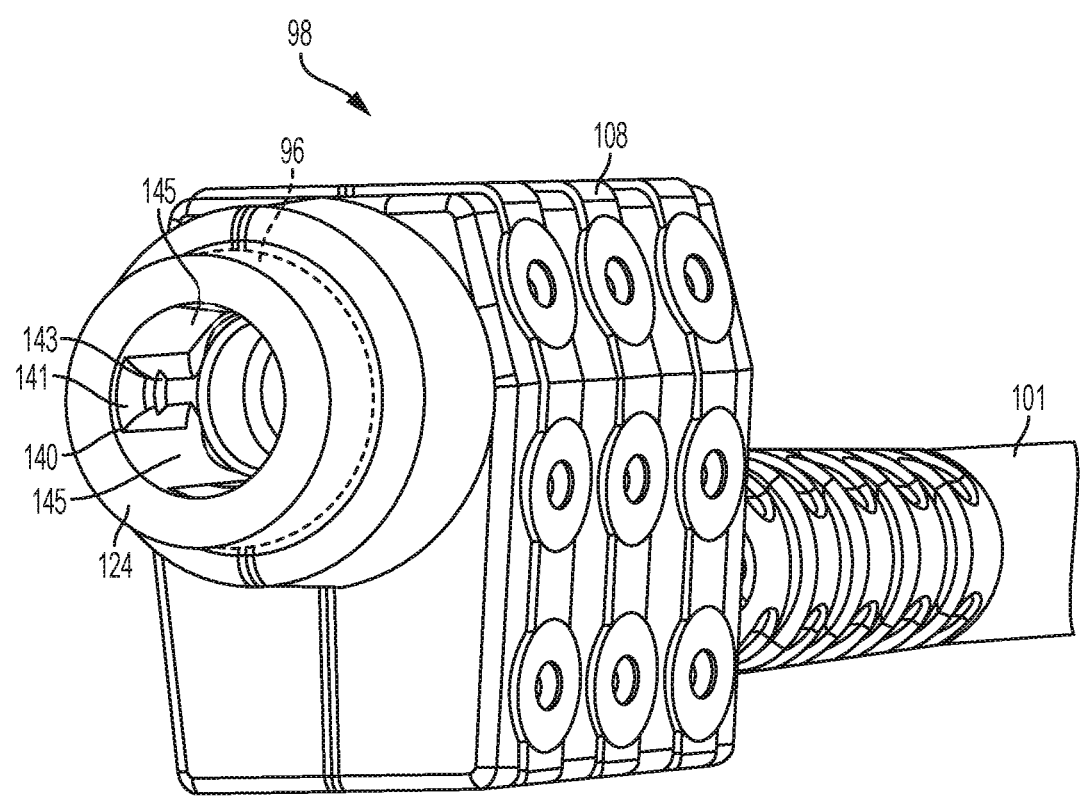
FIG. 8 is a perspective view of a second complementary connector with a protective over-mold in accordance with a non-limiting exemplary embodiment.

FIGS. 7D and 7E illustrate the first complementary connector 50 with a fluid resistant cover 150 according to another embodiment. In this embodiment, the fluid resistant cover 150 is formed as front surface that surrounds the pressurizing device 72, so as to form an annular opening between the cover 150. When the first complementary connector is connected with the second complementary connector 98, the cover 150 can surround at least portions of the proximal coupler 96, and thereby fluidly isolate components of the first complementary connector 50 and the second complementary connector 98. While the illustrated embodiments of FIGS. 7B-7E show the fluid resistant cover 150 provided on the first complementary connector 50, it should be understood that the fluid resistant cover 150 can also be provided on the second complementary connector (e.g., surrounding the proximal coupler 96 so as to fluidly isolate components of the first and/or second complementary connectors).

Aspects of the aforementioned embodiments may also be employed with a "dual charge" connector system. For instance, while the aforementioned description focuses on a catheter arrangement having a single fluid column being charged by a single connector assembly (including the first complementary connector 50 and second complementary connector 98), such embodiments may also be employed to charge two separate fluid columns with a single connector assembly. Specifically, a connector assembly is configured such that a single stroke of the first complementary connector into the receiving well of the second complementary connector can result in a charging event for two fluid columns that may not be in fluid communication with one another. In such cases, similar principles with respect to the displacement of fluid contained within the receiving well of the second complementary connector into monitor lumens extending into the first complementary connector (as described with reference to FIGS. 1-8) are utilized. Advantageously, such embodiments rely on fewer components and connections to charge the balloons, as will be described below.

Figure 9:
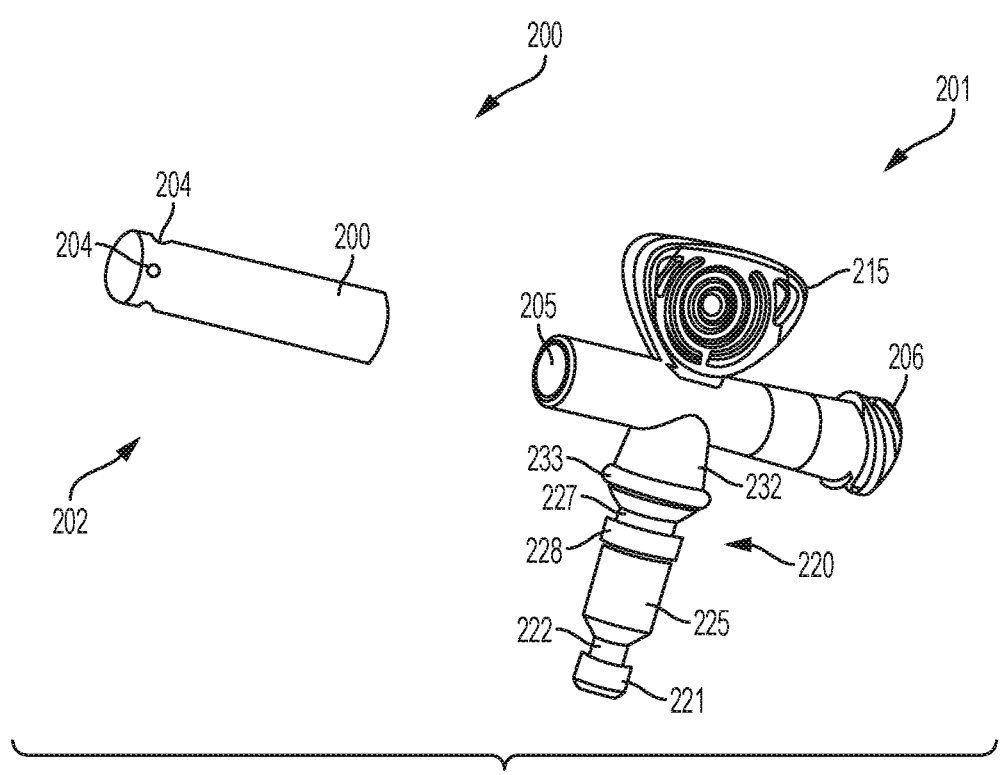
FIG. 9 is a perspective view of a first complementary connector on a proximal end of a catheter and a distal end of a catheter in accordance with a non-limiting exemplary embodiment.
Figure 10:
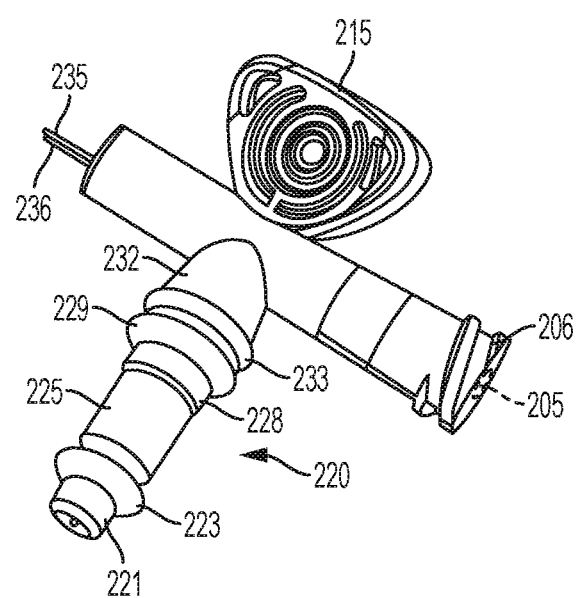
FIG. 10 is a perspective view of a first complementary connector on a proximal end of a catheter in accordance with a non-limiting exemplary embodiment.
Figure 11:
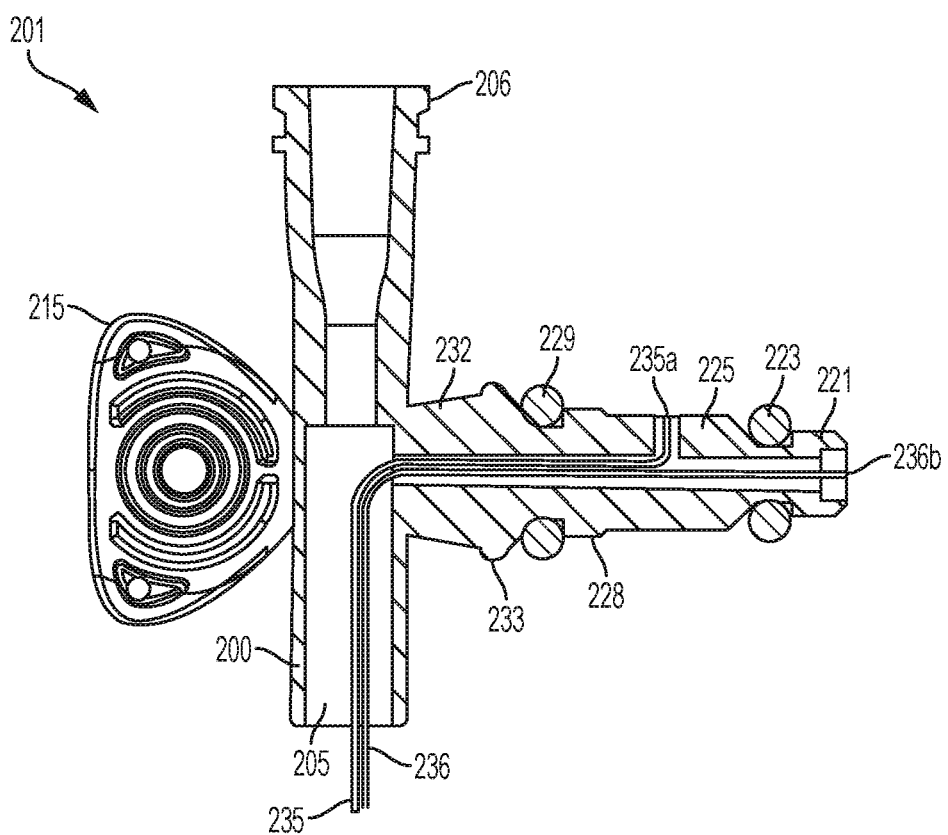
FIG. 11 is cross sectional side view of a first complementary connector on a proximal end of a catheter in accordance with a non-limiting exemplary embodiment.

FIGS. 9-11 illustrate a first complementary connector connected to a multi-lumen catheter according to another embodiment. Advantageously, the embodiment of FIGS. 9-11 may permit charging more than one catheter balloon independently using a single first complementary connector and second complementary connector, as will be described below. With reference to FIG. 9, the multi-lumen catheter 200 has a hollow tube 210 and a central lumen 205 that extends from a proximal end 201 of the catheter 200 to a distal end 202 of the catheter 200. The central lumen 205 is in fluid communication with one or more holes or apertures 204 on the distal end 202 of the catheter 200. The central lumen 205 is operatively coupled and longitudinally aligned with an end connector 206 disposed on the distal end 202 of the catheter 200.

In a non-limiting example, the end connector 206 comprises a luer connector which is a standardized connector system for fluid fittings used to make substantially leak-free connections between mating complementary fluid connectors used in medical and laboratory instruments, including hypodermic syringe tips and needles or stopcocks and needles. While a luer connector is specifically referenced herein, other suitable connectors used to minimize fluid leakage is contemplated herein. Advantageously, the end connector 206 and direction of fluid aspiration and/or infusion through central lumen 205 can be collinear with a longitudinal axis of the central lumen 205 so as to decrease frictional resistance to aspiration and/or infusion forces acting on the catheter 200.

While a dual balloon system is not shown in FIGS. 9-10, it is generally shown in FIG. 1 and described in greater detail above. However, the dual balloon system described above discloses two or more separate charging connector assemblies for each pressure sensing balloon (if two or more balloons are used). Aspects of the present disclosure allow for a dual balloon system to be charged with a single connector assembly, such as those illustrated in FIGS. 9-11.

Referring again to FIG. 9, in a non-limiting exemplary embodiment, a tab 215 is disposed about a side surface of the catheter 200 near a proximal end 201 of the catheter 200. The tab 215 is generally triangular (though other shapes may be used) with an overall planar construction. A front and back side of the tab 215 comprise indentations to provide a gripping surface, which, in an example can be graspable by the thumb and/or index finger of a medical practitioner. The tab 215 facilitates the medical practitioner to hold a proximal end 201 of the catheter 200 during use of the catheter described further herein. In some such cases the tab 215 can permit the medical practitioner to push a pair of complementary connectors to "charge" the multi-balloon system and measure pressure changes within the body of the patient.

With continued reference to FIG. 9, and referring now to FIGS. 10 and 11 illustrate various views of the catheter assembly 200. As seen therein, a first complementary connector 220 can be disposed on the distal end 202 of the catheter 200 opposite the tab 215. The first complementary connector 220 can be generally cylindrical, though other shapes are contemplated within the scope of the present disclosure. The first complementary connector 220 comprises a pressurizing device 221 (e.g., piston or plunger) located on the distal end of the first complementary connector 220. An annular groove 222 (best seen in FIG. 9) is disposed adjacent the pressurizing device 221 and is configured to receive a resilient annular member 223 (e.g., a rubber O-ring or other resilient member) therein. The first complementary connector 220 further comprises a neck 225 disposed adjacent the annular groove 222. The neck has a diameter greater than the diameter of the pressurizing device 221 and the first annular groove 222. A second annular groove 227 (shown in FIG. 9) is disposed adjacent the neck 225 and opposite the first annular groove 222. The second annular groove 227 has a diameter greater than the first annular groove 222 and is also configured to receive a resilient annular member 229 thereon.

In another aspect, the relative diameters of the two grooves 222, 227 are substantially similar. However, the outside diameter of the O-ring 223 placed on the second annular groove 227 is greater than the outside diameter of the O-ring 229. In examples where the different annular resilient members 223, 229 have a different outside diameter, once placed in the two grooves 222, 227, the annular resilient members 223, 229 are capable of engaging inside surfaces of different sized chambers and function to create a dual charge action. A collar 228 is disposed about neck 225 and adjacent O-ring 229 to stabilize the O-ring 229 about the first complementary connector 220.

With continued reference to FIG. 11, the first complementary connector 220 further comprises a stem 232 disposed adjacent the second O-ring 229. The stem 232 is integrally formed with the catheter 200 and comprises a rigid annular protrusion 233. In addition, the first complementary connector 220 comprises two monitor lumens 235, 236 disposed about a longitudinal axis of the first complementary connector 220. Each of the monitor lumens 235, 236 are independent of one another. For instance, each monitor lumen 235, 236 may not be in fluid communication with one another and may extend through the catheter 200 from a distal end 202 to a proximal end 201. Further, each monitor lumen 230 may be in fluid communication with a balloon disposed on a distal end 202 of the catheter 200.

As described elsewhere herein, the internal volume of a monitor lumen and balloon together define a fluid (e.g., air) column used to measure changes in pressure within the body of a patient. In a non-limiting exemplary embodiment, the proximal end 235a of monitor lumen 235 terminates at a side surface of the first complementary connector 220 and, in one aspect, in the neck 225 of the first complementary connector 220. The proximal end 236a of monitor lumen 236 terminates at the face of pressurizing device 221.

Figure 12:
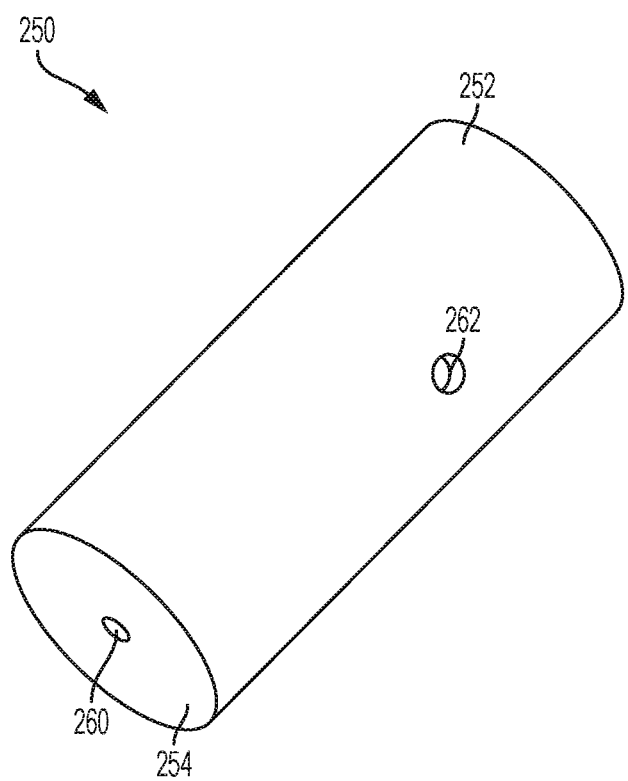
FIG. 12 is a perspective view of a second complementary connector in accordance with a non-limiting exemplary embodiment.
Figure 13:
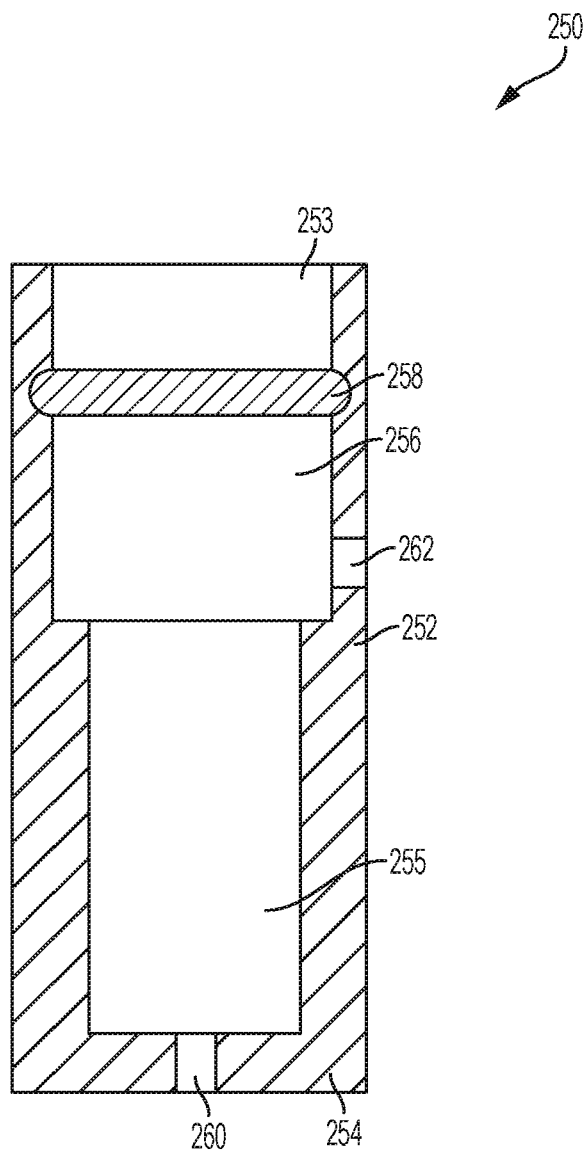
FIG. 13 is a cross sectional side view of a second complementary connector in accordance with a non-limiting exemplary embodiment.
Figure 14:
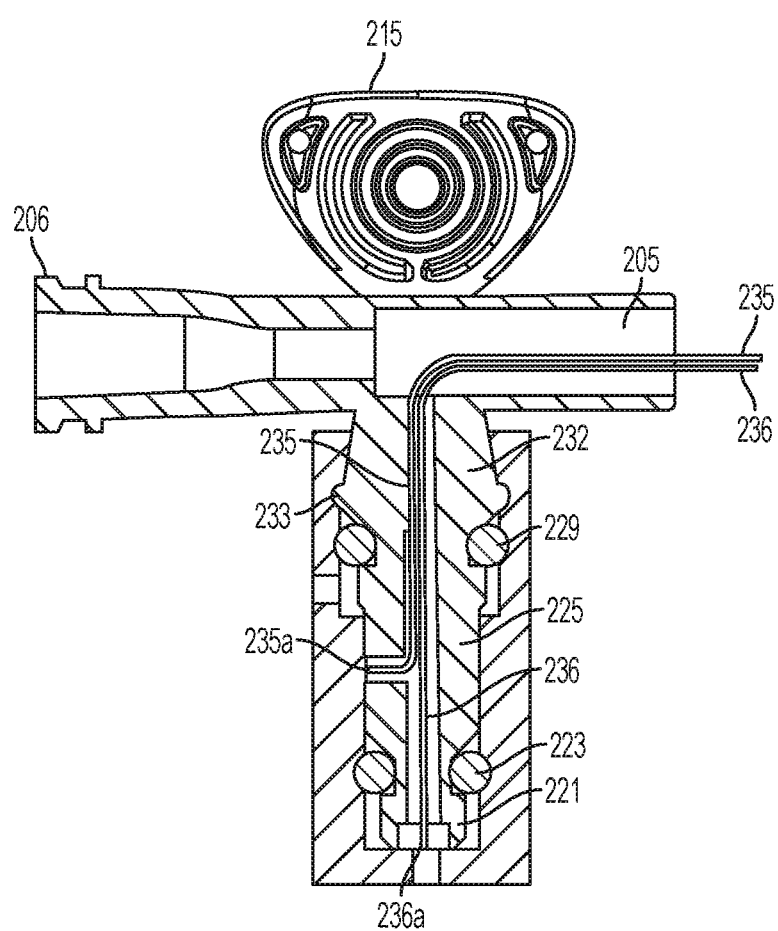
FIG. 14 is a cross sectional side view of a second complementary connector disposed within a second complementary connector in accordance with a non-limiting exemplary embodiment.

FIGS. 12 and 13 illustrate a second complementary connector 250 for engaging with the first complementary connector 220. As disclosed previously, such engagement may permit "charging" of the pressure sensing balloon. With reference to FIGS. 12-13, the second complementary connector 250 comprises a generally cylindrical housing 252 comprising a central receiving well with two internal chambers. The cylindrical housing 252 comprises an open mount 253 and an enclosed bottom 254. A first chamber 255 is located at the bottom of the receiving well and a second chamber 256 is located at the top of the receiving well.

As perhaps best seen in FIG. 13, in a non-limiting exemplary embodiment, the first chamber 255 has an inner diameter smaller than an inner diameter of the second chamber 256. The first chamber has a longitudinal length greater than a longitudinal length of the second chamber 256. An annular groove 258 is disposed within the second chamber 256 and is configured to receive a portion of the rigid annular protrusion 233 of first complementary connector 220 therein in an effort to secure the first complementary connector 220 within the second complementary connector 250. While an annular groove 258 is disclosed as part of the mechanism to secure the connector assembly together, it is understood that other mechanisms may be employed, including the raised platform arrangement 140 disclosed above.

In certain non-limiting exemplary embodiments, as seen in FIG. 13, the second complementary connector 250 comprises a first pressure port 260 disposed in the bottom of cylindrical housing 252. The first pressure port is in fluid communication with the first chamber 255. A second pressure port 262 is disposed in a sidewall of the cylindrical housing 252 and is in fluid communication with the second chamber 256. The two different pressure ports are each coupled to a different pressure detection device (not shown) such as a pressure transducer or other suitable pressure sensing mechanism for detecting changes in pressure within the fluid columns. For instance, each pressure port is in fluid communication with a separate fluid column, each fluid column being defined by a monitor lumen (e.g., 235 or 236) and internal volume of a corresponding balloon.

FIGS. 14, 15A, 15B and 15C illustrate the arrangement of the pressure ports within the different chambers 255, 256 in fluid communication with distinct fluid columns of the first complementary connector 220 and catheter 200 which provide for independent charging of each balloon by way of the fluid columns of the first complementary connector 220 and the second complementary connector 250 assembly.

Figure 15A:
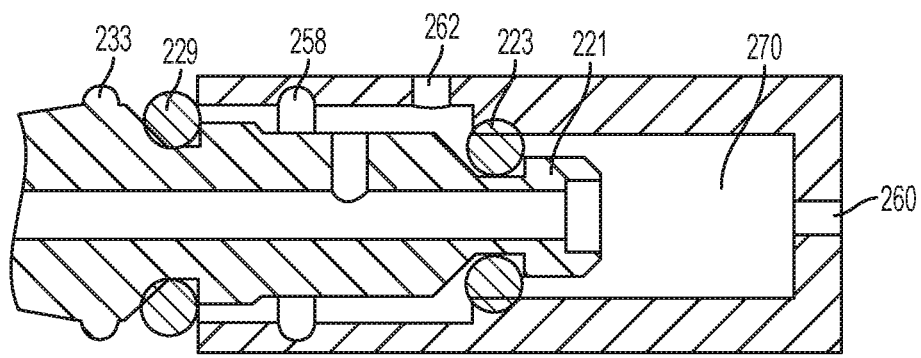
FIGS. 15A, 15B and 15C are a cross sectional side views of a first connector as it is being disposed within a second complementary connector in accordance with a non-limiting exemplary embodiment.

With reference to FIG. 15A, as the pressurizing device 221 of first complementary connector 220 is inserted into the first chamber 255 of the second complementary connector 250, the first O-ring 229 engages the inner sidewall of the first chamber 255 to create a sealed environment comprising the first charge volume 270. At this point, the second O-ring 229 has not fully engaged the sidewall of the second chamber 256 and thus no sealed charge volume associated with the second chamber 256 has been created.

Figure 15B:
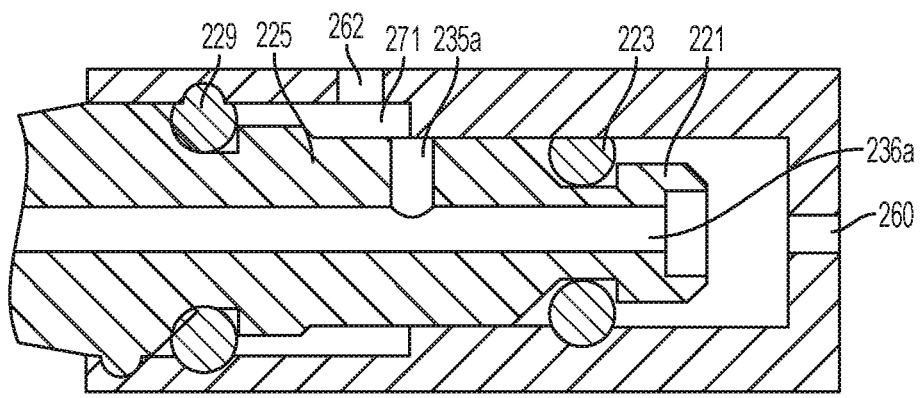

As shown in FIG. 15B, as the pressurizing device 221 is advanced further into the first chamber 255, a portion of the first charge volume 270 is "charged" or introduced into the fluid column associated with monitor lumen 236. The second O-ring 229 engages the sidewall of the second chamber 256 as it engages annular groove 258 (or raised platform 140, described previously) creating a seal in the second chamber 256 and thus creating a second charge volume 271.

Figure 15C:
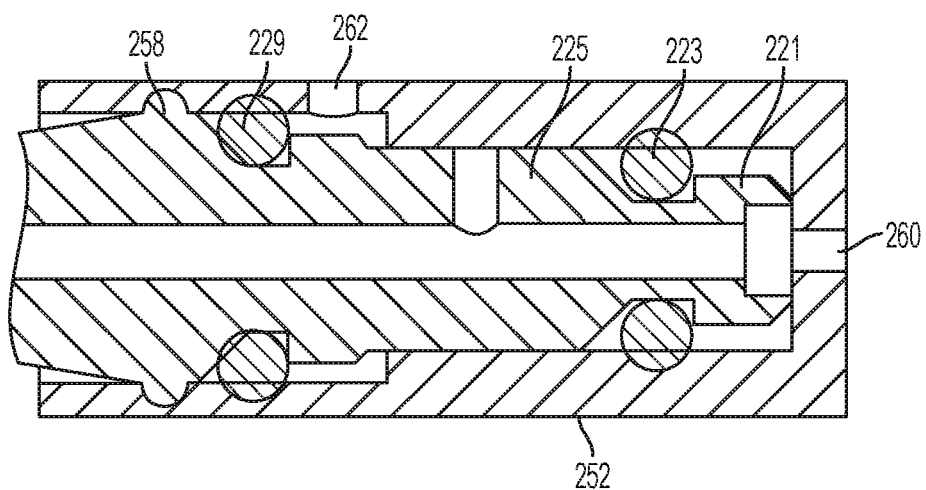

Referring to FIG. 15C, as the pressurizing device 221 is advanced further into the first chamber 255, the remaining volume of the first charge volume 270 is charged into the fluid column associated with monitor lumen 236 and the entirety of the second charge volume 271 is charged or loaded into the fluid column associated with monitor lumen 235. A space between the sidewall of the first chamber and the distal end of monitor lumen 235a further facilitates loading the second charge volume 271 into the fluid column associated with monitor lumen 235.

In some such examples, the first complementary connector 220 can be constructed such that as the pressurizing device 221 completes its full "stroke" within the second complementary connector 250, the first charge volume 270 is loaded or introduced into the fluid column associated with monitor lumen 236, the second charge volume is loaded or introduced into the fluid column associated with monitor lumen 235, and the rigid annular protrusion 233 is seated within annular groove 258. Thus, two fluid columns are independently charged and can be independently monitored with a single connector assembly.

In a non-limiting exemplary embodiment, the relative charging volume of each of the first and second charging volumes 270, 271 can be substantially similar. However, in another aspect, the relative charging volumes can be different as suits a particular purpose. For example, in a non-limiting exemplary embodiment, different charging volumes may be used to accommodate different balloon sizes. In another aspect, however, the balloons may be sized to be substantially similar but different charge volumes are used in order to compare and contrast the results of testing within the cavity of the body at different charge volume ranges. In one non-limiting example, the first and second charge volumes range from 20 microliters to 90 microliters.

In some such embodiments, the second complementary connector 250 may be used with either a single charge first complementary connector 50 (e.g., such as those illustrated in FIGS. 2-3) or a dual charge first complementary connector 220 depending on the geometry of the first complementary connector. For instance, according to certain embodiments, a single second complementary connector (e.g., 98 or 250) may be used in connection with a catheter having a first complementary connector (e.g., 50 or 220) with a single monitor lumen (e.g., as seen in FIG. 2-3) or with two monitor lumens (e.g., as seen in FIG. 9-11).

Figure 16:
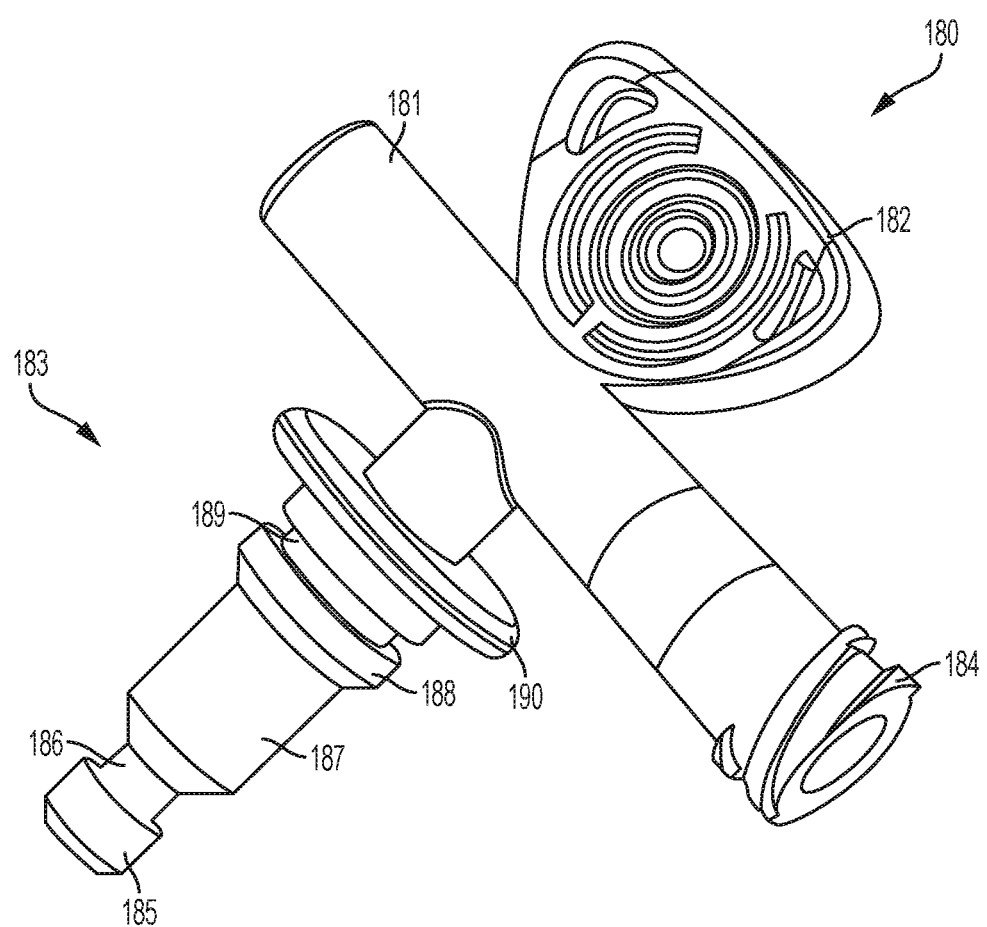
FIG. 16 is a perspective view of a first complementary connector in accordance with a non-limiting exemplary embodiment.

FIG. 16 illustrates a connector assembly 180 in accordance with a non-limiting exemplary embodiment, substantially similar to the connector assembly illustrated in FIGS. 9-11. As seen from FIG. 16, the connector assembly 180 may be useful for inline infusion or aspiration of a fluid, as will be described further below. The connector assembly 180 is coupled to or integrally formed with the body 181 of a catheter (not shown) and is disposed on the proximal end of the catheter. In one aspect, the connector assembly 180 comprises a T-shaped connector having a tab 182 on a first side of the catheter body 181 disposed opposite a cylindrical first complementary connector 183. The body 181 of the catheter is disposed between the tab 182 and cylindrical first complementary connector 183 forming the T-shape.

With continued reference to FIG. 16, an extreme proximal end of the catheter body 181 comprises a luer connector 184 or other connection mechanism for coupling to an intravenous drip (or other fluid source) or a syringe which may be used both to aspirate or infuse fluids through the catheter. The cylindrical first complementary connector 183 comprises a pressurizing device 185 (e.g., piston or plunger) at its distal end adjacent an annular groove 186. The annular groove 186 can be configured to receive a resilient annular member (not shown) therein.

A neck 187 is adjacent the annular groove 186. A collar 188 is disposed adjacent the neck 187 and comprises a second annular groove 189 configured to receive an optional second resilient annular member (not shown). A rigid annular protrusion 190 is disposed above the collar 188. In a non-limiting exemplary embodiment, the first complementary connector 183 is configured to be inserted into a second complementary connector (e.g., the second complementary connectors referenced and described herein) and displace a volume of fluid within the second complementary connector into a monitor lumen disposed within the first complementary connector 183 similar to the function of the cylindrical first complementary connector described above.

In some embodiments, however, the rigid annular protrusion 190 is sized to have an outer diameter greater than the other diameter of the first complementary connector 183 and approximates the face 124 of the engagement section 123 of a second complementary connector 98 (see, e.g., FIG. 5). The T-shaped geometry provides a direct line for infusion/aspiration of fluids into luer connector 184 and the lumen associated with the catheter body 181. In this manner, the resilient annular member that would be disposed in groove 189 can act as a seal for the connector assembly 180 and the rigid annular groove acts as a stop and "cap" to enclose the first complementary connector 183 within its attendant second complementary connector. In another aspect, there is no resilient annular member disposed within groove 189. Rather, the groove 189 is available to seat a disc or other sliding mechanism more fully described below and shown in FIGS. 17A-17C.

While the connection interface between the complementary connectors described above comprises an enclosed system without many moving components, some examples include use of a biased clasp disposed about the second complementary connector to secure the first complementary connector therewithin.

Figure 17A:
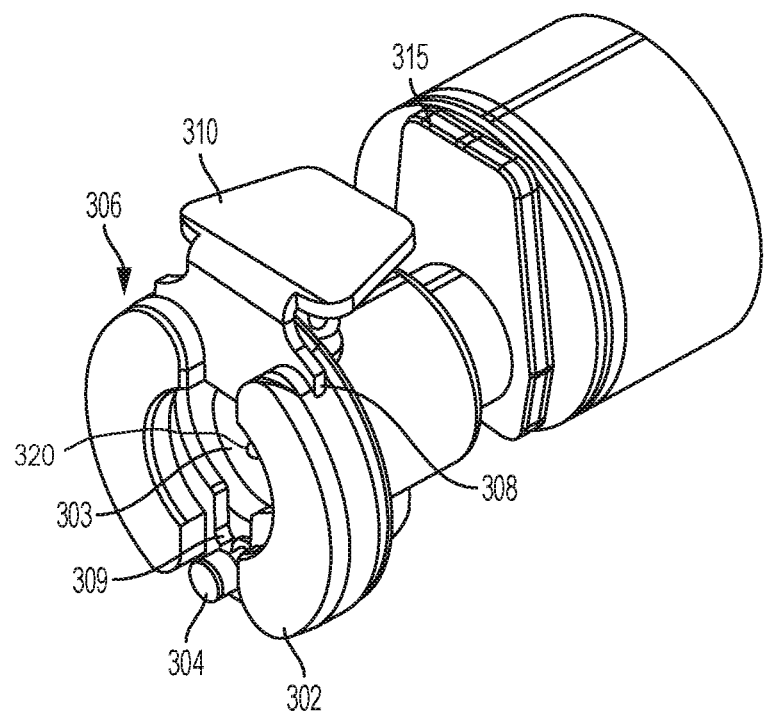
FIGS. 17A, 17B and 17C are different views of a second complementary connector in accordance with a non-limiting exemplary embodiment.
Figure 17B:
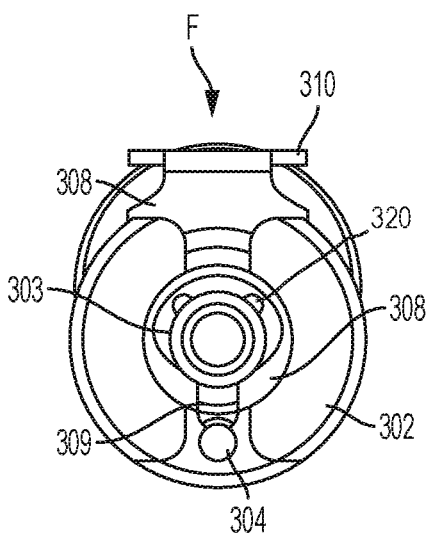
Figure 17C:
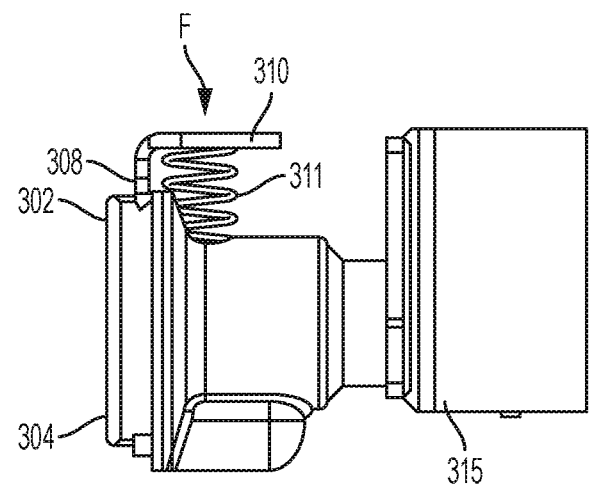

FIGS. 17A-C illustrate different views of a second complementary connector 300 which may be used having either a single chamber or dual chamber construction as described herein to charge a single monitor first complementary connector or a dual monitor first complementary connector depending on the specific geometry of the first complementary connector. The second complementary connector 300 comprises a face 302 coupled to an engagement section 303. The engagement section 303 can receive and engage a first complementary connector therein and permit charging a monitor lumen with a predetermined charge volume of fluid as has been described herein.

Continuing with FIG. 17C, a biased locking clasp 306 is disposed between the face 302 and engagement section 303 of the second complementary connector 300. The clasp 306 comprises a flat, annular disc 308 coupled to a tab 310. A biasing member (e.g., a spring or other resilient device) 311 can be positioned between the tab 310 and an outside wall 312 of the central receiving well and biases the disc 308 in a "locked" position. A post or locking pin 304 extends outward from the engagement section 303 and is positioned within a slot 309 of the disc 308. The post 314 secures the bottom of the disc 308 about the engagement section 303 of the second complementary connector 300 and limits the displacement of the disc 308 from the biasing force of the spring 311.

As seen in FIGS. 17A and 17B, a plurality of vents 320 may be provided in (or surrounding) the engagement section 303. Vents 320 may provide a similar function to vents 145 described herein. For instance, vents 320 may reduce the chances of overcharging a balloon of a catheter connected (e.g., by way of a first complementary connector) to the second complementary connector 300. In some such cases, the first complementary connector can have O-rings (80, 223, 229, etc.) that may be received within a corresponding recessed portion of the engagement section 303 (as described with respect to embodiments illustrated in FIGS. 2-6 and 9-15c).

With continued reference to FIGS. 17A-17C during connection of the first complementary connector (according to any embodiment disclosed herein) with the second complementary connector 300, fluid may be displaced (for instance, from within the engagement section 303) by a pressurizing device (e.g., 72, 221, etc.) as it passes a side surface of the engagement section 303. In such cases, fluid displaced by the pressurizing device may be vented through the vent 320. Further, in some such cases, the balloons 40 may not be charged (e.g., by displacement of fluid) until an adequate fluid seal between the first complementary connector and the second complementary connector is established, for instance, until a resilient member (e.g., O-ring 80, 223, 229 etc.) of the first complementary connector engages at a predetermined axial position on the side surface of the engagement section 303. Accordingly, the specific volume of fluid to properly "charge" the balloon 40 is introduced into the fluid column thereby reducing the chances of overcharging the balloon 40.

In a non-limiting exemplary embodiment, a user holds the second complementary connector 300 in one hand and with the thumb (or some other finger) depresses tab 310 in direction F. As the tab 310 is depressed, the disc 308 slides downward exposing a substantial part of the engagement section 303 to allow insertion of a first complementary connector (e.g., 72, 183 or 220). The user then inserts a first complementary connector into the central receiving well. Once it is fully inserted, the user releases the tab 310 and the spring 311 biases the disc 308 upward until it engages with a surface on the first complementary connector (e.g., annular groove 189 in FIG. 16, etc.) to retain the first complementary connector therein. The second complementary connector is coupled to a pressure detection device enclosed in a cable assembly 315 as described more fully herein.

Figure 18A:
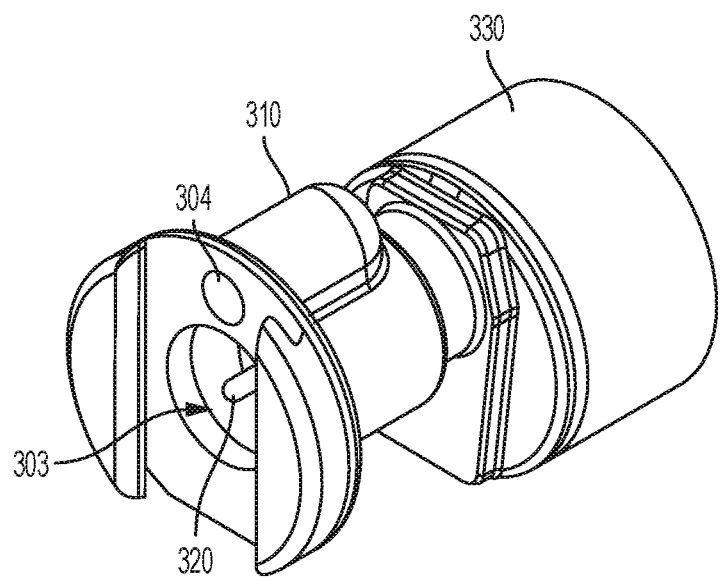
FIGS. 18A, 18B, 18C and 18D are different views of a second complementary connector in accordance with a non-limiting exemplary embodiment.
Figure 18B:
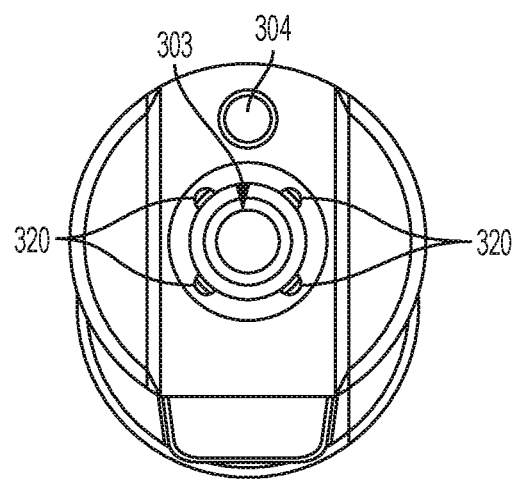
Figure 18C:
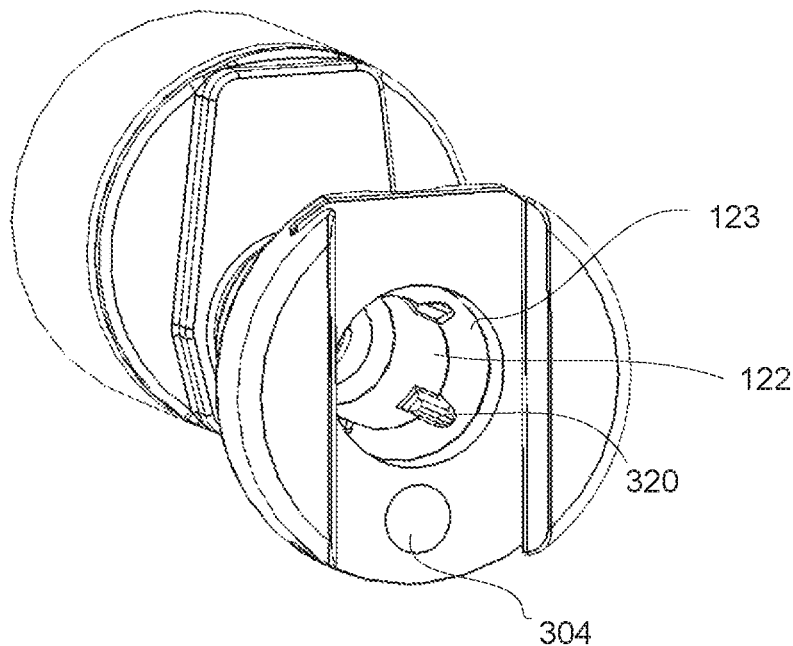
Figure 18D:
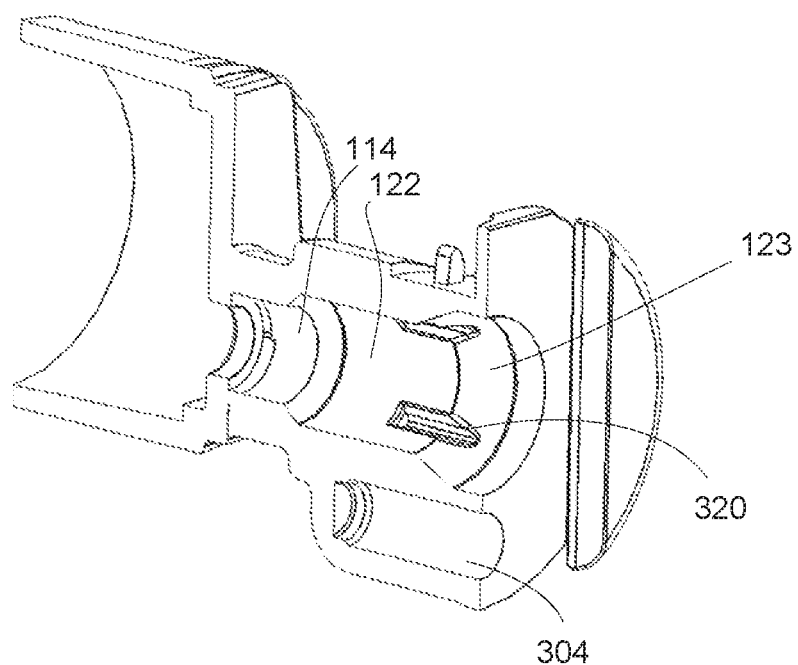

FIGS. 18A-18D illustrate another second complementary connector substantially similar to that illustrated in FIGS. 4-8 and 17A-17C, where like reference numerals indicate like components and/or functionality, with the differences described below. FIGS. 18A and 18B show a second complementary connector with a more rounded housing 330 of the second complementary connector that can be formed as a single molded component. The components and operation of the second complementary connector of FIG. 18A-18D, however, is substantially similar to those described with respect to FIG. 17A-17C.

Various examples have been described. These and other examples are within the scope of the following claims.

The invention claimed is:

1. A connector apparatus for a pressure sensing catheter, the pressure sensing catheter comprising one or more hollow pressure compliant members, comprising:
   a first complementary connector in fluid communication with the one or more hollow pressure compliant members, the first complementary connector having an aligning portion and a charging portion along a central axis of the first complementary connector with a resilient member located between the aligning portion and the charging portion, the aligning portion having a cross-sectional area, normal to the central axis, and less than a cross-sectional area normal to the central axis of the charging portion;
   a second complementary connector having a proximal coupler with an alignment section and a charging section along a central axis thereof, the alignment section having a cross-sectional area complementary to the cross-sectional area of the aligning portion to receive the aligning portion therein, the charging section having a cross-sectional area complementary to receive the charging portion and the resilient member therein and form a fluid tight seal therebetween,
   the first complementary connector being configured to displace a predetermined volume of fluid, from within the proximal coupler into the one or more hollow pressure compliant members when the alignment section receives the aligning portion, the charging section receives the charging portion, and the resilient member forms the fluid tight seal within the charging section; and
   a pressure detection device fluidly coupled to the one or more hollow pressure compliant members so as to detect a pressure associated with the one or more hollow pressure compliant members wherein the proximal coupler comprises an engagement section, the engagement section having a cross-sectional area complementary to an engagement portion of the first complementary connector and one of the engagement portion and the engagement section has a protrusion; and
   the other of the engagement portion and the engagement section has a front surface leading to a complementary recess for frictionally receiving the protrusion after the front surface has engaged the protrusion, the front surface forming a reduction in the cross-sectional area of the other of the engagement portion and the engagement section leading to the complementary recess such that the protrusion encounters the reduction in the cross-sectional area prior to encountering the complementary recess, the recess enclosing the protrusion within the other of the engagement portion and the engagement section, the protrusion and recess forming a snap fit to frictionally engage and retain the first complementary connector within the second complementary connector when the protrusion and recess are aligned.

2. The connector apparatus of claim 1, wherein the first complementary connector comprises a monitor lumen disposed about a longitudinal axis of the first complementary connector.

3. The connector apparatus of claim 1, wherein the engagement section comprises a plurality of channels defined therein.

4. The connector apparatus of claim 3, wherein each channel of the plurality of channels is oriented normal to a longitudinal axis of the second complementary connector.

5. The connector apparatus of claim 4, wherein the engagement portion of the first complementary connector comprises a protrusion received within at least one channel of the plurality of channels.

6. The connector apparatus of claim 3, each channel of the plurality of channels is circumferentially spaced apart from another channel of the plurality of channels.

7. The connector apparatus of claim 6, wherein the plurality of channels are disposed within a raised platform comprising a tapered front end and tapered sides.

8. The connector apparatus of claim 3, wherein the cross-sectional area of the charging section is complementary to the cross-sectional area of the charging portion to receive the charging portion therein.

9. The connector apparatus of claim 1, wherein the engagement section has a cross-sectional area greater than the cross-sectional area of the alignment section and the charging section.

10. The connector apparatus of claim 1, wherein the resilient member has a first axial length and the charging section has a second axial length greater than the first axial length, to permit the resilient member to slide axially relative to the charging section when received within the charging section.

11. The connector apparatus of claim 1, wherein the pressure detection device is positioned so as to be in coaxial alignment with the aligning portion when the first complementary connector is connected to the second complementary connector.

12. The connector apparatus of claim 1, further comprising a fluid resistant cover provided on the first complementary connector, the fluid resistant cover generally surrounding and thereby fluidly isolating at least the pressure detection device when the first complementary connector is connected to the second complementary connector.

13. The connector apparatus of claim 1, wherein the resilient member has a cross-sectional area, normal to the central axis of the first complementary connector, greater than the cross-sectional area of the charging section.

14. A connector apparatus for a pressure sensing catheter, the pressure sensing catheter comprising one or more hollow pressure compliant members, comprising:
- a first complementary connector in fluid communication with the one or more hollow pressure compliant members, the first complementary connector having a charging portion supporting a resilient member;
- a second complementary connector having a proximal receptacle with a charging section and a vent section along a central axis thereof, the charging section having a cross-sectional area, normal to the central axis, complementary to the resilient member to receive the resilient member therein and form a fluid tight seal therebetween, the vent section having a cross-sectional area, normal to the central axis, complementary to the resilient member to receive the resilient member therein, the vent section including one or more vents permitting fluid flow within the one or more vents when the resilient member is received in the vent section;
- the first complementary connector being configured to displace a predetermined volume of fluid, from within the proximal receptacle, into the one or more hollow pressure compliant members when the charging section receives the resilient member; and
- a pressure detection device fluidly coupled to the one or more hollow pressure compliant members so as to detect a pressure associated with the one or more hollow pressure compliant members
- wherein the proximal receptacle comprises an engagement section, the engagement section having a cross-sectional area complementary to an engagement portion of the first complementary connector and one of the engagement portion and the engagement section has a protrusion tapering in a direction along a central axis thereof; and the other of the engagement portion and the engagement section has a front surface leading to a complementary recess for frictionally receiving the protrusion after the front surface has engaged the protrusion, the front surface forming a reduction in the cross-sectional area of the other of the engagement portion and the engagement section leading to the complementary recess such that the protrusion encounters the reduction in the cross-sectional area prior to encountering the complementary recess, the protrusion and recess forming a snap fit to frictionally engage and retain the first complementary connector within the second complementary connector when the protrusion and recess are aligned.

15. The connector apparatus of claim 14, wherein the first complementary connector comprises a monitor lumen disposed about a longitudinal axis of the first complementary connector.

16. The connector apparatus of claim 14, wherein the engagement section comprises a plurality of channels defined therein.

17. The connector apparatus of claim 16, wherein each channel of the plurality of channels is oriented normal to a longitudinal axis of the second complementary connector.

18. The connector apparatus of claim 17, wherein the engagement portion of the first complementary connector comprises a protrusion received within at least one channel of the plurality of channels.

19. The connector apparatus of claim 16, each channel of the plurality of channels is circumferentially spaced apart from another channel of the plurality of channels.

20. The connector apparatus of claim 19, wherein the plurality of channels are disposed within a raised platform comprising a tapered front end and tapered sides.

21. The connector apparatus of claim 14, wherein the engagement section has a cross-sectional area greater than the cross-sectional area of the alignment section and the charging section.

* * * * *